United States Patent
Mayer et al.

(10) Patent No.: US 10,136,880 B2
(45) Date of Patent: *Nov. 27, 2018

(54) ASSEMBLY FOR AUGMENTING HARD TISSUE

(71) Applicant: Woodwelding AG, Stansstad (CH)

(72) Inventors: Jörg Mayer, Niederlenz (CH); Marcel Aeschlimann, Ligerz (CH)

(73) Assignee: WOODWELDING AG, Stansstad (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,806

(22) Filed: Oct. 17, 2017

(65) Prior Publication Data

US 2018/0035989 A1 Feb. 8, 2018

Related U.S. Application Data

(62) Division of application No. 14/406,816, filed as application No. PCT/CH2013/000101 on Jun. 12, 2013, now Pat. No. 9,808,229.

(Continued)

(51) Int. Cl.
| | |
|---|---|
| *A61B 17/68* | (2006.01) |
| *A61F 2/30* | (2006.01) |
| *A61B 17/88* | (2006.01) |
| *A61B 17/00* | (2006.01) |
| *A61C 8/00* | (2006.01) |

(Continued)

(52) U.S. Cl.
CPC ...... *A61B 17/00491* (2013.01); *A61B 17/686* (2013.01); *A61B 17/8822* (2013.01); *A61C 8/0016* (2013.01); *A61C 8/0018* (2013.01); *A61C 8/0089* (2013.01); *A61F 2/30734* (2013.01); *A61B 17/0401* (2013.01); *A61B 2017/00004* (2013.01); *A61B 2017/005* (2013.01); *A61F 2/44* (2013.01);

(Continued)

(58) Field of Classification Search
CPC ... A61C 8/0016; A61C 8/0018; A61C 8/0089; A61B 17/686; A61B 17/8822; A61B 17/00491

See application file for complete search history.

(56) References Cited

U.S. PATENT DOCUMENTS 7,335,205 B2 2/2008 Aeschlimann et al.
9,808,229 B2 * 11/2017 Mayer .............. A61B 17/00491

(Continued)

FOREIGN PATENT DOCUMENTS

WO 2008/034276 3/2008
WO 2010/045751 4/2010

(Continued)

*Primary Examiner* — Christopher Beccia
(74) *Attorney, Agent, or Firm* — Rankin, Hill & Clark LLP

(57) ABSTRACT

An augmentation method is provided, wherein a thermoplastic augmentation element is subject to mechanical energy impact and mechanical pressure by a tool so that augmentation material of the augmentation element is liquefied and pressed into hard tissue to augment the hard tissue, wherein in at least one axial depth, the augmentation element is segmented as a function of the circumferential angle so that at this axial depth the circumferential wall of the initial opening in first regions is in contact with the augmentation element and in second regions is not in contact with the augmentation element.

19 Claims, 9 Drawing Sheets

Related U.S. Application Data

(60) Provisional application No. 61/659,663, filed on Jun. 14, 2012.

(51) Int. Cl.
    *A61F 2/44*     (2006.01)
    *A61B 17/04*     (2006.01)

(52) U.S. Cl.
    CPC ............ *A61F 2002/30065* (2013.01); *A61F 2002/30556* (2013.01)

(56) References Cited

U.S. PATENT DOCUMENTS

| | | |
|---|---|---|
| 2010/0023057 A1 | 1/2010 | Aeschlimann et al. |
| 2010/0241229 A1 | 9/2010 | Baehre et al. |
| 2011/0160870 A1 | 6/2011 | Baumgartner et al. |
| 2012/0129131 A1 | 5/2012 | Baehre et al. |
| 2012/0157977 A1 | 6/2012 | Hulliger |
| 2012/0328360 A1 | 12/2012 | Koppitz et al. |

FOREIGN PATENT DOCUMENTS

| | | |
|---|---|---|
| WO | 2010/072009 | 7/2010 |
| WO | 2010/127462 | 11/2010 |
| WO | 2012/141813 | 10/2012 |

* cited by examiner

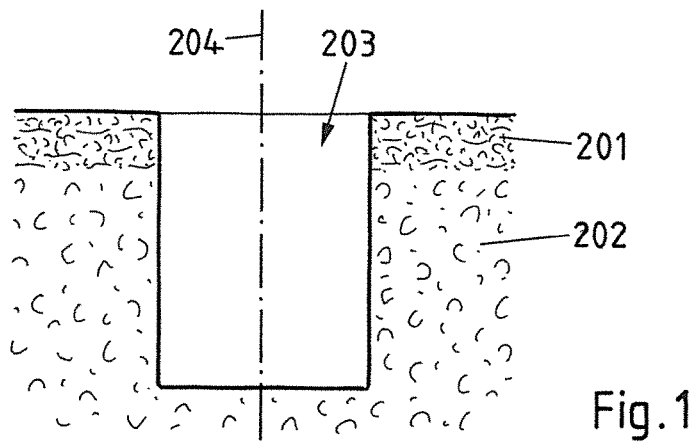
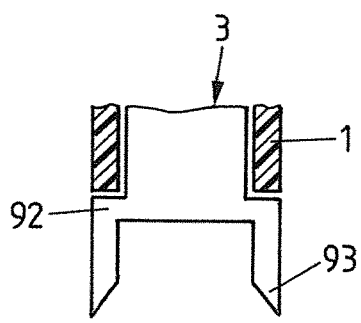
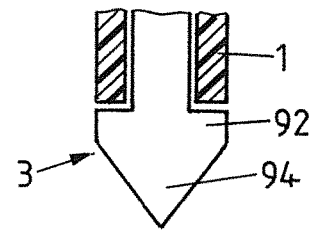
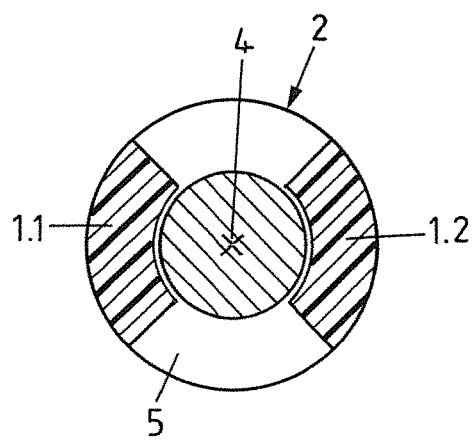
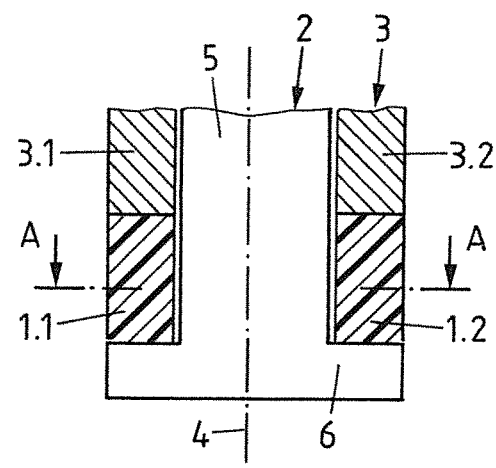

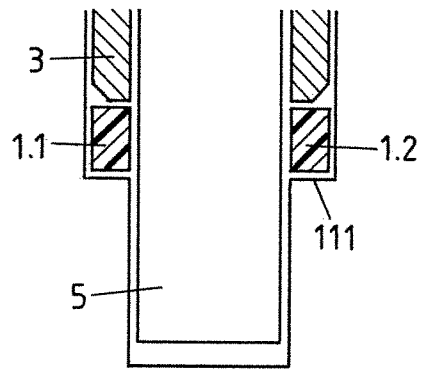
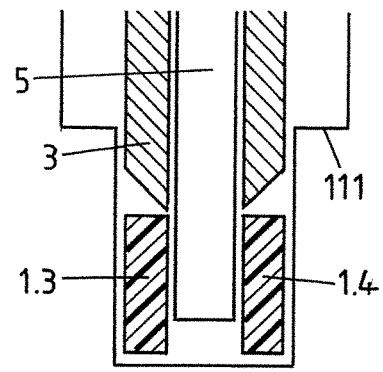
Fig. 7a    Fig. 7b
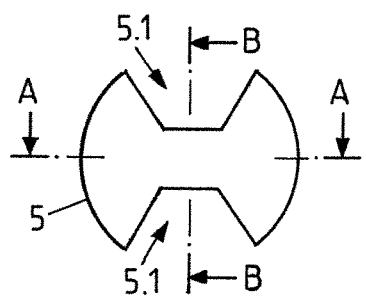
Fig. 7c
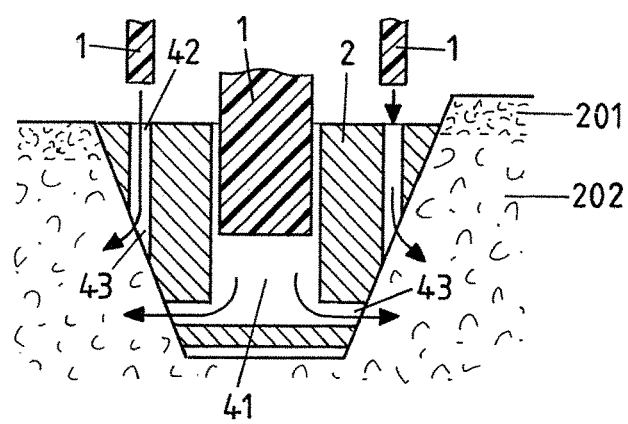
Fig. 8

ASSEMBLY FOR AUGMENTING HARD TISSUE

BACKGROUND OF THE INVENTION

Field of the Invention

The invention is generally in the field of medical technology and, in particular, relates to medical devices, medical apparatus and medical methods, and especially to implants, apparatuses for implantation, and implantation methods.

Description of Related Art

If screws are anchored in live bone tissue, for example of the vertebrae, the mandible, the maxilla (for dental implants) or other bone tissue, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or osteopenic or otherwise weakened bone tissue.

WO2010/045751 discloses a method of anchoring an implant in hard tissue and/or hard tissue replacement material. The method includes compressing a thermoplastic augmentation element between a tool and a counter element while mechanical energy is coupled into the tool so that thermoplastic material of the augmentation element is liquefied and pressed into surrounding tissue. In this process, for compressing the augmentation element a tensile force is coupled into the tool, and the tool is pulled towards a proximal direction.

While this method is advantageous in many situations, it is restricted to situations where the tool may be introduced into a comparably large initial opening.

SUMMARY OF THE INVENTION

It is an object of the present invention to provide methods for improved anchoring stability of surgical implants in bone tissue. It is a particular object to provide a method of augmenting hard tissue and/or hard tissue replacement material for later insertion of a surgical implant, such as a surgical screw or an implant weldable to the augmentation material. It is a further object of the present invention to provide according devices. It is yet another object to provide implantation methods that include augmenting the tissue.

In accordance with a first aspect of the invention, a method of augmenting hard tissue and/or hard tissue replacement material for insertion of an implant, an according device, and an implantation method including such an augmenting method are provided.

In accordance with the method of the first aspect the augmentation method includes the steps of:

providing an initial opening in the hard tissue and/or hard tissue replacement material;

providing a thermoplastic augmentation element and a tool;

placing the augmentation element in the initial opening, placing the tool in contact with an end face of the augmentation element and pressing the tool against the end face while energy is coupled into the tool and while a periphery of a liquefaction interface of the tool and the augmentation element is within the opening;

thereby liquefying material of the augmentation element at the liquefaction interface(s) to yield liquefied material;

causing portions of the liquefied material to penetrate into structures of the hard tissue and/or hard tissue replacement material;

allowing the liquefied material to harden and to thereby become augmentation material; and removing the tool;

wherein at least one of the following conditions is fulfilled:

a. in at least one axial depth, the augmentation element is segmented as a function of the circumferential angle so that at this axial depth the circumferential wall of the initial opening in first regions is in contact with the augmentation element and in second regions is not in contact with the augmentation element;

b. in at least one axial depth of a resulting, augmented opening, the augmentation material is caused to be segmented as a function of the circumferential angle;

c. in a resulting, augmented opening, the augmentation material is provided in at least two augmented regions axially spaced from each other, wherein between the two augmented regions there is a non-augmented region;

d. the augmentation element does not have the symmetry of a rotational cylinder but is asymmetric with respect to rotation around any axis.

Also according to the first aspect of the invention, an assembly including the augmentation element and the tool is provided, the assembly being capable of carrying out the above-defined method.

Therein, the end face of the augmentation element may be a proximal end face, and in the step of pressing the tool against the end face while energy is coupled into the tool, the tool may be pressed towards a distal direction against the proximal end face of the augmentation element.

In accordance with an alternative version (in a 'rearward' configuration), the end face of the augmentation element may be a distal end face, the tool may include a proximally facing shoulder, and in the step of pressing the tool is pressed towards a distal direction, i.e. the tool is pulled (a tensile force is coupled into the tool).

In rearward configurations (this pertains to all embodiments and aspects of the invention in which a tensile force is coupled into the tool), especially if the energy coupled into the tool is mechanical vibration energy, the tool may include a cable and a distal element attached to the cable, the distal element forming a proximally-facing coupling-out face that may interface with a distally-facing distal coupling-in face of the augmentation element. Such a configuration makes possible to augment tissue also in situations where access with stiff tools would be difficult, and deflections of the mechanical energy become possible. According embodiments are yet described in more detail referring to the fifth aspect of the present invention. Similarly, also radiation energy can be deflected in this manner, if the cable includes or forms at least one flexible radiation conductor.

In the present text, embodiments of the first aspect as well as of the hereinafter described second aspect are sometimes referred to as embodiments of segmented augmentation.

After removal of the tool, there will be an augmented opening in the hard tissue/hard tissue replacement material, in which opening an implant may be anchored in a later step. The augmented opening may correspond to the initial opening, with a potential slight reduction of the cross section due to augmentation material anchored in lateral walls of the initial opening. In alternative embodiments, further steps of modifying the initial opening may be part of the method so that the augmented opening, at least in certain axial depths (especially at more proximal positions) has a larger cross section than the initial opening. In many embodiments, however, the augmented opening will not be substantially larger than the initial opening.

In examples of the first aspect, an auxiliary element that may also serve as a counter element is used to guide the augmentation element and/or to exert a counter force. The auxiliary element may, for example, include a guiding shaft and a distal broadening (foot) that forms a shoulder facing to the proximal side so that a distal end face of the augmentation element may be pressed against the shoulder when the tool is pressed against the distal direction.

In condition a., the second regions are substantial. For example at least 60°, or at last 100° or even at least 180° of the overall circumference is taken up by the second regions. Condition a. implies that the surface comprises, in addition to first regions with augmentation material, also extended second regions without augmentation material.

In condition a., according to an option, the segmentation is such that it goes along a substantial part of its axial length, for example along at least 50% of its axial length. It may go essentially along the full axial length of the augmentation element, i.e. there are circumferential angles that are free of augmentation material (or, where there is no contact between the circumferential wall and the augmentation element) along the full axial length. Especially, the augmentation element may include segments that are entirely separate from each other. Alternatively, such segments may be connected by bridge portions connecting them for example at the proximal end and/or the distal end. Such bridge portions may be chosen to be unsubstantial, i.e. the amount of material of the bridge portions may be chosen to be by far lower than the material between the bridge portions (for example less than 5% or less than 3% or 2% of the total amount).

In condition b. the distribution between augmented and not augmented regions along the circumference is determined by the method and the used devices, i.e. is systematic. This means that the used devices and/or the used method are chosen so that segmentation is achieved in a purposeful manner; in most cases (unless anatomy prevents this) the surgeon can influence where the augmented and non-augmented regions are finally to be by choosing an appropriate orientation around an augmentation axis.

A method satisfying condition b. may, according to a first possibility, achieved by using a segmented augmentation element according to condition a. In accordance with a second possibility, the initial opening that is made prior to the step of causing liquefied augmentation material to penetrate into the hard tissue and/or hard tissue replacement material, may have a geometry different from the geometry of the augmented opening. The initial opening may for example have a different symmetry than the augmented opening. The step of causing liquefied augmentation material to penetrate into the hard tissue and/or hard tissue replacement material may then include causing the liquefied material to penetrate into lateral walls of the initial opening, in a segmented or non-segmented manner. Subsequently to this step, a further (in addition to making the initial opening) material removing, for example drilling step is made, in which tissue with augmentation material is removed, so that the augmented opening satisfies condition b. For example, the augmentation element and tools used (such as a sonotrode and possibly a guiding element for the augmentation element) may have an according, non-circular symmetry.

The augmented opening resulting after augmentation may thus, according to a first possibility, be the initial opening with tissue/tissue replacement material provided by the augmentation material in the augmented regions. In accordance with a second possibility, which can be combined with the first possibility, the resulting opening may be caused by drilling into the initial opening that has tissue/tissue replacement material provided with augmentation material. For example, the initial opening may be such as to not have rotational symmetry with respect to an opening axis, and after the process of pressing the augmentation material into the tissue, a further opening forming step (for example, a drilling step) may be made so that tissue with the augmentation material is removed in certain regions. The further opening forming step may be made by means of a tool that makes circular cylindrical bores, such as a drill.

Condition b. may, for example, be achieved either by a segmented sonotrode, by material removal in accordance with the second possibility above, or by other means such as using a plurality of augmentation elements and prior to or after forming the opening.

For condition c., the augmentation process, for example as described hereinbefore (with or without segmentation) or described hereinafter or described in WO 2010/045751 incorporated herein by reference in its entirety may be carried out at different axial depths. Alternatively, an auxiliary element having an opening accessible from the proximal side and with material exit holes may be used, wherein the material exit holes define the locations where the tissue is augmented. Other variants are possible.

Axial segmentation in accordance with condition c. has the advantage that the augmentation process may be adapted to particular physiological boundary conditions. Also, the regions that are not augmented may provide a faster healing, depending on the tissue quality.

In accordance with condition d., the augmentation element may especially have an outer contour shape (in a cross section perpendicular to the axis) that is essentially triangular, rectangular, star-shaped, etc. (all with rounded corners) etc. Circumferential segmentation (to satisfy condition b.) may be achieved by subsequently drilling, in accordance with the second aspect described hereinafter, a cylindrical hole, the drill having a diameter greater than a minimal outer diameter of the augmentation element but smaller than a maximal outer diameter of the augmented tissue/tissue replacement material.

All of the conditions a.-d. can be combined with each other, i.e. ab, ac, ad, bc, bd, cd, abc, abd, acd, bcd, and abcd.

In accordance with a second aspect, the augmentation method of augmenting hard tissue and/or hard tissue replacement material includes the steps of:

Providing at least one thermoplastic augmentation element;

Placing the augmentation element in contact with the hard tissue and/or hard tissue replacement material and causing mechanical energy to impinge on the augmentation element to liquefy at least portions of the augmentation element and causing liquefied augmentation material portions of the augmentation element to penetrate into the hard tissue and/or hard tissue replacement material;

Letting the liquefied augmentation material portions re-solidify;

Removing a portion of the hard tissue and/or hard tissue replacement material and of the re-solidified augmentation material, whereby an augmented opening is obtained, the augmented opening having surface portions of the hard tissue and/or hard tissue replacement material with the re-solidified augmentation material and having surface portions of the hard tissue and/or hard tissue replacement material without the re-solidified augmentation material.

The removing step may be made by means of a tool that makes circular cylindrical bores, such as a drill.

In a first group of embodiments, prior to the step of causing liquefied augmentation material to penetrate into the hard tissue and/or hard tissue replacement material, an initial opening of a geometry different from the geometry of the augmented opening is provided, the initial opening for example having a different symmetry than the augmented opening. The step of causing liquefied augmentation material to penetrate into the hard tissue and/or hard tissue replacement material may then include causing the liquefied material to penetrate into lateral walls of the initial opening. For example, the augmentation element and tools used (such as a sonotrode and possibly a guiding element for the augmentation element) may have an according, non-circular symmetry.

The subsequent step of removing a portion of the hard tissue and/or hard tissue replacement material and of the re-solidified augmentation material then may divide the augmentation material into segments, the surface portions of the hard tissue and/or hard tissue replacement material without the re-solidified augmentation material being between the segments.

In a second group of embodiments, the augmentation element or a plurality of augmentation elements may be caused to be anchored in the tissue by a method as described in U.S. Pat. No. 7,335,205, which is incorporated herein by reference in its entirety. For example, a plurality of essentially pin-like augmentation elements may be used. The augmentation elements are anchored at positions that are peripheral with respect to the later added augmented opening. Thereafter, the augmented opening is made, the augmented opening, for example, being cylindrical or conical or having an elliptical or any other shape.

In embodiments of the first and/or second aspect, the initial opening and/or the final, augmented opening may be stepped, i.e. its cross section may vary as a function of the depth, with a step-like dependency of the cross section on the axial position.

Embodiments of the first and/or second aspect of the invention may provide the following advantage: A non-segmented augmentation with a contiguous, tube-shaped augmentation element would lead to a toroidal augmentation material distribution in the bone material. If subsequently a screw is screwed into the augmented initial opening, the material will bear a substantial resistance, and this may lead to a torsional movement of the whole toroidal augmentation material ring within the bone tissue leading to a damage to the trabeculae of the cancellous bone. In contrast thereto, the segmented augmentation material can give way to some extent due to the residual elasticity of the bone tissue, and this will ease screwing in of the screw, while the additional stability provided by the augmentation can be benefited from.

In accordance with a third aspect of the invention, a method of augmenting hard tissue and/or hard tissue replacement material is provided, which method including augmenting the tissue after implantation of the implant. To this end, after implantation of the implant (for example conventionally, by drilling a hole and thereafter pressing or screwing the implant into the hole; or by a method as disclosed in U.S. Pat. No. 7,335,205), at least one augmentation element is anchored, under the impact of energy, in the tissue to be in contact with the implant. The implant and the augmentation element may, in accordance with a first possibility, include structures so that they serve as base part and based part in the sense of the teaching of US 2010/0 023 057 incorporated herein by reference in its entirety so that the implant and the augmentation element interlock after the process. In accordance with a second possibility, the implant and the augmentation element both include thermoplastic material so that the augmentation element is weldable to the implant.

In accordance with the method of the fourth aspect, the augmentation method includes the steps of:
  providing an initial opening in the hard tissue and/or hard tissue replacement material;
  providing a thermoplastic augmentation element (for example being a sleeve with a sleeve wall), and further providing a tool (for example sonotrode) and an auxiliary element;
  placing the augmentation element in the initial opening, the augmentation element at least partially encompassing a guiding portion of the tool or of the auxiliary element,
  coupling a pressing force and energy into the tool and from the tool into the augmentation element while a portion of the augmentation element is within the opening and in contact with the hard tissue and/or hard tissue replacement material;
  thereby liquefying material of the augmentation element to yield liquefied material;
  causing portions of the liquefied material to penetrate into structures of the hard tissue and/or hard tissue replacement material and/or into structures of an element connected to the hard tissue and/or hard tissue replacement material;
  allowing the liquefied material to harden and to thereby become augmentation material; and
  removing the tool;
  wherein at least one of the following conditions is fulfilled:
   A. during the step of coupling a pressing force and energy into the tool, an outer protection element at least partially encompasses the tool and locally prevents the tool from being in contact with the hard tissue and/or hard tissue replacement material;
   B. the augmentation element is generally sleeve-shaped and includes at least one indentation or hole in a sleeve wall;
   C. during the step of coupling a pressing force and energy into the tool, in a telescoping region a portion of the tool encompasses a portion of the auxiliary element or a portion of the auxiliary element encompasses the tool, wherein the tool and/or the auxiliary element comprises/include at least one protrusion facing to the auxiliary element/tool, respectively, so that in the telescoping region a contact between the tool and the auxiliary element is prevented, except for the protrusion/protrusions;
   D. during the step of coupling a pressing force and energy into the tool, the tool is pressed towards the distal direction, and wherein the tool includes a distal broadening forming an salient feature that prevents a contact between the tool and the hard tissue and/or hard tissue replacement material at locations proximally of the salient feature (i.e. the diameter of the tool is, except for the salient feature, reduced compared to the diameter of the initial opening);
   E. prior to the step coupling a pressing force and energy into the tool, the augmentation element is connected to the tool by an axial positive-fit connection, and during the step of coupling a pressing force and energy into the tool, the auxiliary element is pressed against a distal direction to activate the step of liquefying material of the augmentation element and to push portions of the liquefied material aside and into the structures of the hard tissue and/or hard tissue replacement material.

At least the following combinations of these conditions are possible and are further embodiments of the invention: AB, AC, ABC, BC, BD, BCD, CD, CDE, DE. In addition, in special configurations also BE, BCE, and BCDE are possible.

In this, as well as in the other aspects of the invention, the energy may be coupled into the tool (and from there into the augmentation element) in the form of mechanical vibrations.

Alternatively, the energy may be coupled into the tool by way of radiation (especially laser radiation) that is absorbed by the augmentation element. As yet another alternative, the energy may be mechanical energy different from mechanical vibration, for example rotation. As an even further alternative, the energy may be heat, for example directed to the augmentation element by heat conduction and/or by causing an electrical current to flow through the augmentation while the latter includes electrically conducting material with a relatively high electrical resistance.

In embodiments in which the energy coupled into the augmentation element is radiation energy, the tool has waveguiding properties and is equipped for coupling the radiation into the augmentation element. The tool may, for example, be an optical fiber or a bundle of optical fibers or may have integrated light guiding elements. The augmentation element in these embodiments is equipped for absorbing the radiation coupled into it, either at the interface or in the augmentation element body, or both. To that end, the augmentation element may be of an essentially transparent material, provided with pigments, or similar absorbing the radiation.

In condition A, the outer protection element may be a sleeve of a suitable material and having suitable surface properties to minimize friction between the tool and the protection element. Especially, it may be a thin sleeve, the material thickness being merely sufficient so that the protection element is dimensionally stiff. The protection element prevents the tool from being in contact with the tissue locally, at the place of the protection element. At other places, direct contact between tool and tissue may occur depending on the situation.

In condition A, optionally the protection element may include thread tapping functionality.

In condition B, the augmentation element may be generally sleeve-shaped but with the indentations, holes or the like being systematic weakenings. Due to these weakenings—that may be arranged as spaces adapted to the purpose of the augmentation element and/or the anatomical circumstances of the tissue to be augmented—the augmentation material may be liquefied with less energy impact. Onset of liquefaction as a function of the power that impinges on the augmentation element is already at lower powers, so that less power is required to liquefy. In embodiments, the weakenings are grooves that are inclined with respect to a radial direction. The grooves define necks in the augmentation element material at which the liquefaction sets in when energy impinges. After liquefaction at the necks (or other weak points), the remaining pieces may be subject to a shear movement along the direction defined by the grooves. In embodiments, the grooves are such that the more proximal portions are pressed outwardly when the tool presses them towards the distal direction.

In this, the holes may, for example, be arranged to form axially-oriented slits or axially-oriented rows of separate holes.

In embodiments of all aspects, the surface of the tool (for example sonotrode if the energy impinges through mechanical vibration) that is in contact with the augmentation element and through which the mechanical energy is coupled into the augmentation element may be generally flat (radial, i.e. perpendicular to the proximodistal axis) or may be tapered or have any other shape. A particularly advantageous combination is the combination of an augmentation element fulfilling condition B. with a flat tool contact face. One reason for this is that the design and handling of the tool is easier when the surface is flat, while the advantages of non-flat contact faces (namely, direct, targeted onset of liquefaction, displacement of the liquefied material into the tissue) can be achieved also if condition B. is fulfilled.

In condition C, in the telescoping region (where the tool and the auxiliary element are in sliding contact), the tool may include inward projections, such as (axial and/or circumferential) ridges, spheres, etc. In addition or as an alternative, the auxiliary element may include corresponding outward projections. Due to these projections, a volume (buffer volume) remains between the tool and the auxiliary element so that, with the exception of the protrusions, they do not touch each other. This reduces energy loss, noise (if the energy is mechanical energy, for example vibration energy) and impinging on the tissue. The protrusions may be such that liquefied material does not penetrate into the buffer volume. This may, for example, be ensured that any remaining gap between the sonotrode and the auxiliary element at the interface to the augmentation element is small enough so that surface tension and heat flow induced quenching of the polymer prevents liquefied material from entering into such a gap. Typically, the upper limit for the gap size is 0.05 to 0.1 mm for polymer of low melt viscosity (e.g. amorphous, polylactides, i.e. p-L-DL-lactide 70/30 (Resomer LR706, Evonik Germany) or up to 0.2 mm for polymer with a higher melt viscosity (e.g. p-LLA (Resomer L210, Evonik Germany)). The optimal gap width can be determined in simple size variation experiments.

From the above, it follows that it is often advantageous if the gap is smaller than 0.2 mm so that surface tension prevents liquefied material from entering into such a gap.

Especially, in an embodiment the tool includes an inwardly protruding distal circumferential ridge. In another embodiment, the tool and/or the auxiliary element includes a plurality of axial ridges or a plurality of micro-protrusions that may be calotte-shaped, conical or have other shapes, including identical and different shapes.

In condition D, the tool comprises, in addition or as an alternative to the protrusions defined by condition C, at least one outward protrusion that keeps a body of the tool from getting in direct contact with the tissue. Especially, such outward protrusion may be located essentially at the distal end of the tool and at the interface to the auxiliary element to thereby prevent liquefied material from flowing back along the tissue instead of being pressed into the tissue.

Like in all other embodiments, the feature of condition D may be combined with a slanted distal tool surface.

In condition E, the positive-fit connection may for example be provided by an outer thread of the tool or by circumferentially running indentations onto which the augmentation material was cast during the manufacturing process. When proceeding in accordance with condition E., the surgeon may advance the auxiliary element into the distal direction, while the tool is held still, slowly retracted towards the proximal direction, or slowly moved into the distal direction also (slower than the auxiliary element).

Condition E features the first advantage that due to the configuration with the central tool and the peripheral auxiliary element, there is only minimal contact between the tool and the tissue surrounding the initial opening. It features the further advantage that the augmentation element is coupled to the tool. Therefore, if the energy is mechanical energy, the augmentation element is subject to the full (vibratory, rotational) movement—in contrast to configurations where the tool for example 'hammers' onto the augmentation element. This brings about an additional reduction of the noise caused, as well as of energy required for liquefaction. Also in embodiments where the energy is not mechanical energy but for example radiation energy or heat, the direct contact may be advantageous, especially for optimizing the desired energy transfer into the augmentation element.

If the energy is mechanical vibration energy, the tool is a sonotrode for coupling the mechanical vibrations and/or heat absorbed from these vibrations into the augmentation element.

In addition or as an alternative, other measures for noise reduction may be taken. As an example, the material of the sonotrode and/or the auxiliary element may be chosen so that it may not form a resonating body but is—given the chosen frequencies and dimensions, to be considered as an essentially stiff body (i.e. the wavelength of the vibrations in the body is substantially larger than its dimensions). An example of such a material is PEEK instead of a metal. Other examples include further high temperature melting polymers like Polytetrafluoroethylene (PTFE), polyimides, etc.

In accordance with a fifth aspect of the invention, a device for deflecting mechanical oscillations is used to cause a sonotrode to oscillate, which sonotrode serves as a tool for coupling energy into the augmentation element in an augmentation process. In this, the augmentation process may especially include:

providing an initial opening in the tissue;
providing the augmentation element, and providing a tool;
placing the augmentation element in the initial opening,
    placing the tool in contact with a face of the augmentation element and pressing the tool against the face while vibration energy is coupled into the tool and while a periphery of a liquefaction interface of the tool and the augmentation element is within the opening;
thereby liquefying material of the augmentation element at the liquefaction interface(s) to yield liquefied material, causing a relative movement of the tool with respect to the augmentation element, and causing portions of the liquefied material to penetrate into structures of the tissue;
allowing the liquefied material to harden and to thereby become augmentation material; and
removing the tool.

In embodiments, at the liquefaction interface a full cross section of the augmentation element is liquefied.

The augmentation element may be essentially sleeve-shaped with an axial lumen.

In accordance with the fifth aspect of the invention, the mechanical vibrations the oscillations are deflected from oscillations along a first axis at an oscillation generating apparatus (which for example includes an ultrasonic transducer) to oscillations along a second axis at a location of the tool where it forms the interface.

According to a first option, to this end an arrangement for carrying out the method includes a solid oscillation deflector. This oscillation deflector may be an oscillation element that is elongate and bent between two ends and on which a coupling-in point and a coupling-out point are arranged, such that the oscillation element oscillates transversally at the coupling-in point and at the coupling-out point, when the coupling-in point is subject to an oscillation. Alternatively, this oscillation deflector may be a ring resonator with a coupling-in point and a coupling-out point at different locations on the ring.

According to a second option, the tool includes a flexible, bendable region, namely a cable that deflects the mechanical oscillations. In accordance with this option, the force for pressing the tool against the interface to the augmentation element is coupled into the tool as a tensile force, i.e. the method is carried out in a rearward configuration. In addition to the cable, tool also includes a foot coupled to the cable, the foot forming a proximally-facing face that serves as the coupling-out face of the tool that during the process is in contact with a distal face of the augmentation element, so that the coupling-out face and the distal face together form the interface.

In this text, the term "cable" is not meant to be restricting as to the material or the structure. Especially, the cable may be a wire, a wire rope, a filament, etc., all of a metal, or alternatively of a different material suitable for forming a cable.

In embodiments of the second option, the axial lumen of the augmentation element then is through-going with the cable reaching through the axial lumen.

In addition to the tool, the arrangement for carrying out the method also includes a diverting feature for the cable, such as a reel or a rounded diverter edge. The cable is guided along this diverting feature.

The diverting feature may especially be mounted to the vibration generating apparatus (especially to a housing thereof).

More particularly, the vibration generating apparatus may include a vibration generating module, for example with a piezoelectric transducer, for generating the vibrations (for example ultrasonic vibrations), a cable attached to the vibration generating module, the vibration generating module being movable along a first moving axis within the housing of the apparatus, which first moving axis may correspond to the first axis of the oscillations (which may be longitudinal oscillations in the cable). The cable exits the housing at an exit location.

The vibration generating apparatus then may further include a diverting feature arranged or arrangeable at a distance to the exit location. The diverting feature may be arranged so that the cable is kept along a straight line from the vibration generating module to the diverting feature, or it may be deflected between the diverting feature and the vibration generating module, for example at the exit location. The diverting feature may be mounted to the housing fixedly, or movably, for example extendibly.

As an alternative to being mounted to the housing, the diverting feature may be present as a separate part, for example a diverting tool held by the operator or an assistant during the process.

From the diverting feature to the foot, the cable is kept stretched along a second, different moving axis, which second axis may correspond to the second axis of the oscillations.

The angle between the first axis and the second axis may be chosen depending on the needs. For dental applications, it is often advantageous if the angle is about 90° or slightly larger than 90° (where the angle is defined so that 180° means "no deflection"), for example between 90° and 125°. For other surgical applications, the angle may be different; also angles smaller than 90° are readily feasible.

The counter element, that serves for applying, for example to the proximal end face of the augmentation element, a counter force to the augmentation element (i.e., the augmentation element is, during the process, compressed between the foot and the counter element), may according to a first option also be mounted to the housing. The apparatus then defines the deflection angle at least approximately.

According to a second option, the arrangement may include a separate counter element. Then, the operator may choose the deflection angle in-situ and adjust it if necessary during the process.

For the process, the vibration generating module is retracted within the housing, whereby the cable is pulled to pull the foot along the second axis. The retracting movement may be carried out manually or automatically, for example with the aid of a spring mechanism or motorized. Thereby, augmentation material of the augmentation element is liquefied, for example, starting at the liquefaction interface and, due to the pulling force being applied, displaced and pressed into the tissue. This may be continued until the entire augmentation element is consumed, or until the operator stops the process. Thereafter, the arrangement is retracted towards the proximal side.

Optionally, the foot may include radially protruding blades that divide the augmented regions into segments, as taught in WO 2010/045 751.

Optionally, the augmentation element may be formed in accordance with condition a. of the first aspect, and/or at least one of conditions b.-d. may be fulfilled. Also, at least one of the conditions A.-E. of the fourth aspects may be fulfilled.

In accordance with the first as well as with the second, third, fourth or fifth aspect of the invention, also a kit of parts / an assembly for carrying out the respective method is provided. The kits of parts include the tool, the augmentation element and (if used for the method) the auxiliary element, these items having properties described hereinbefore and hereinafter referring to the respective methods.

An assembly according to the fifth aspect includes in addition to a tool, an auxiliary element and an augmentation element at least partially encompassing the tool or the auxiliary element also the device for deflecting mechanical oscillations (this includes the possibility that the tool itself serves as the oscillation deflector).

In accordance with a sixth aspect of the invention, an initial opening is made by a set-up in which a vibrating tool (sonotrode) or a counter element is also used as hole forming instrument. In accordance with this aspect, the method comprises
  providing an instrument, the instrument including a distal and with a piercing tip and/or a cutting edge;
  providing a thermoplastic augmentation element;
  placing the instrument with the distal end in contact with the hard tissue and/or hard tissue replacement material and pressing the instrument against the hard tissue and/or hard tissue replacement material to force the instrument into the hard tissue and/or hard tissue replacement material;
  placing the augmentation element in contact with a face of the instrument, the face facing to the proximal side,
  pulling the instrument towards a proximal direction against the augmentation element while energy is coupled into the augmentation element;
  thereby liquefying material of the augmentation element to yield liquefied material;
  causing portions of the liquefied material to penetrate into structures of the hard tissue and/or hard tissue replacement material;
  allowing the liquefied material to harden and to thereby become augmentation material; and
  removing the instrument.

During the forcing step, mechanical energy may be coupled into the instrument. Especially, the instrument may be a vibration tool by which in the step of pulling the energy is coupled into the augmentation element in the form of mechanical vibration energy. Then, the vibration source generating such vibrations may firstly generate mechanical vibrations for reaming tissue (to be precise: hard tissue and/or hard tissue replacement material) in a forward movement of the tool and then for liquefying portions of the augmentation element in a backward movement of the tool.

The invention according to its sixth aspect also concerns an according assembly.

It is readily possible to combine features and embodiments of the different aspects with each other. Especially, embodiments of the forth aspect are advantageously provided with features/conditions that characterize the first, second and third aspects and vice versa. The first aspect also combines well with the second aspects, and in embodiments the method according to the third aspect may be applied in addition to (and subsequently to) the first and/or second aspect.

All of aspects 1-4 can be combined with the fifth aspect, and all of aspects 1-5 (with the possible exception of embodiments of the fifth aspect where the tool includes a cable for deflecting the oscillations) can be combined with the sixth aspect.

For all embodiments of aspects 1, -2, 4, 5 and 6 of the invention, the augmentation step may be followed by a subsequent step of inserting the implant.

The implant may, in accordance with a first option, for example be/include a screw that has an outer thread. The thread may be self-cutting, or previously a thread cutter may be used. The thread engages with corresponding structures in the augmented hard tissue/hard tissue replacement material.

In accordance with a second option, mechanical vibration energy or heat may be used to anchor the joining element in the augmented opening. To this end, in accordance with a first possibility, the joining element may include thermoplastic material weldable to the augmentation material. In accordance with a second possibility, the joining element may include a material that is not liquefiable by being brought to a temperature at which the augmentation material is liquid, and structure with pores, openings or the like capable of making a positive-fit connection with the augmentation material. The first and second possibilities can be combined with each other. Also, it is possible to combine the first and second option, for example by using a metallic screw with a porous surface as a joining element, whereby the thermoplastic lining and/or lining element may penetrate into the pores when the screw is inserted in a heated state, so that after cooling the screw is fixed by a positive-fit connection. Techniques of joining a first (base) part and a second (based) part with each other in this manner are disclosed in WO 2008/034 276 incorporated herein by reference in its entirety.

Mechanical vibration or oscillation suitable for devices and methods according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (tool, for example sonotrode) is, for example, designed such that its contact face oscillates predominantly in the direction of the element axis (longitudinal vibration) and with an amplitude of between 1 and 100 µm, preferably around 10 to 30 µm. Rotational or radial oscillation is possible also.

For specific embodiments of devices, it is possible also to use, instead of mechanical vibration, a rotational movement for creating the named friction heat needed for the liquefaction of the anchoring material. Such rotational movement has preferably a speed in the range of 10,000 to 100,00 rpm.

A further way for producing the thermal energy for the desired liquefaction (for the augmentation process and possibly also for anchoring the joining element) includes coupling electromagnetic radiation into the augmentation element and/or into an element in a vicinity thereof in direct or indirect heat conducting contact with the augmentation element. Especially, a light conductor may be used for this purpose. The light conductor may, for example, be a tube-shaped transparent light conducting tool, for example a hollow cylinder of glass or another (for example, plastic) material that is transparent and has a sufficiently high index of refraction for the used radiation (for example, visible or infrared laser radiation).

In this, absorption preferably takes place within the augmentation material to be liquefied or in the immediate vicinity thereof. Depending on the requirements and the set-up the radiation therein may be absorbed at different places:
   a. in accordance with a first variant, the distal end of the tool may be provided with an absorbing coating or surface so that the distal end of the tool—that interfaces with the augmentation element—is heated, so that the generated heat causes the augmentation element to be liquefied at the interface to the tool.
   b. in accordance with a second variant, the augmentation element is so as to at least partially absorb the radiation. If the augmentation element strongly absorbs the radiation (for example by having a high concentration of a pigment or other absorber or in that the polymer itself absorbs the radiation), absorption will primarily take place at the interface to the tool. In case of weaker absorption (if, for example, the augmentation element has a polymer composition that is transparent for the radiation and a low concentration of absorbing pigments), then absorption will be distributed through at least a part of the length of the augmentation element. Then the tendency will be that after the radiation sets in some time passes until liquefaction starts, but then a substantial portion of the material will be softened already. For special applications, it is possible to have a pre-determined distribution of absorbing pigment in the augmentation element.
      Instead of a pigment or an absorbing polymer or in addition thereto, absorption can be caused by at least one of surface roughness, micro- or nanosized fillers, or admixed components with absorbing capability etc.)
   c. In accordance with a third variant, the augmentation element is also transparent, and the counter element includes an absorbing surface, so that the radiation is primarily absorbed at the interface between the counter element and the augmentation element. In this variant, the step of coupling energy into the augmentation element and simultaneously applying a force often includes advancing the counter element towards the proximal direction while the tool may for example be held still.

Instead of providing the tool in the form of a radiation conductor, or in addition thereto, it is also possible to include a miniature laser (such as a laser diode or an arrangement of laser diodes) directly in the tool.

As an even further alternative to providing the tool in the form of a radiation guiding cylinder, the tool may include any other radiation directing arrangement. This includes the possibility of directing the radiation to a distal foot and causing it to impinge on the augmentation element from the distal side in a "rearward" configuration. For the purpose of radiation directing, the tool may include appropriate means like integrated fiber radiation conductors, mirroring faces, etc.

Preferably, electromagnetic radiation in the visible or infrared frequency range is used, wherein the preferred radiation source is a corresponding laser.

In specific embodiments that include radiation as energy source, parameters and material combinations may be applied as taught in publications teaching techniques of implanting implants that include heat deformable materials and that teach heating these materials by radiation; or publications that teach heating a thermoplastic material for other purposes. Such publications include, for example, US 2012/0157977, US 2011/0160870, US 2012/0328360, WO 2012/141813, US 2012/129131 (including a listing of lasers and teachings of absorption and chromophores/pigments as well as considerations of laser operating conditions and energy considerations including thermal regulation), all incorporated herein by reference.

According to an even further alternative, the energy may be supplied to the system by way of electric heating of one of the device parts.
   a. According to a first possibility, the tool may include a resistance heater in immediate vicinity to the augmentation element, for example directly at the interface. (or, the resistance heater itself may be at some distance to the interface, and the tool includes a heat conductor from the resistance heater to the interface).
   b. In accordance with a second possibility, the tool may include an electrode at the interface to the augmentation element, the augmentation element is a poor electrical conductor, and some other element—for example, the auxiliary/counter element or, if available, a protective sheath element or other—includes a further electrode so that electricity is conducted through the augmentation element and thereby heats the latter. The arrangement of the electrodes in this may influence the location of primary heating. In embodiments, teachings of prior art documents such as US 2010/0241229 relating to resistance heating of electrically conductive polymers and especially the teaching relating to materials and heating operating parameters, may be referred to; US 2010/0241229 being incorporated herein by reference.

In this text the expression "thermoplastic material being liquefiable e.g. by mechanical vibration" or in short "liquefiable thermoplastic material" or "liquefiable material" is used for describing a material including at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are, for example, produced by ultrasonic devices as is known for dental applications. For being able to constitute a load-bearing connection to the tissue, the material has an elasticity coefficient of more than 0.5 GPa, preferably more than 1 GPa. (The material property values mentioned in this text generally refer to room temperature (23° C.) unless referring to temperatures or defined otherwise in this text). The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

However, in applications where only minimal bearing capacity is required (i.e. applications for which the required capability of transferring stress is below 5 MPa or below 1 MPa), the thermoplastic material may also be substantially softer. Especially, due to the liquefaction taking place directly at the interface between the tool and the augmentation element, no mechanical energy has to be transmitted through the element itself. Thus, during the process and thereafter (thus also generally at the temperature at which it is used, for example room temperature) it may be comparably soft, even to the point of being waxy. In other words, the advantages of an elasticity coefficient of at least 0.5 GPa do not apply or are at least not pronounced in these systems. Since the integration of drugs or other biologically active substances often requires very low temperatures, this technique allows the use polymers as drug carriers that have a glass temperature much below 0° C. or even −20° C. or having a very low molecular weight to minimize the energy input to induce melting or polymers with a melting point only slightly above body temperatures, e.g. above 40° C. or 50° C. but below 80° C.

For applications with no or reduced load bearing capacity requirements (for example, below 5 Mpa) even elastomer materials for the augmentation materials may be used, these materials having, for certain applications, advantages in terms of ideal stress distribution, for example in poor, osteopenic bone.

Suitable resorbable polymers are, for example, based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as, for example, polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www-.matweb.com by Automation Creations, Inc.). An overview table of polymers and applications is listed in Wintermantel, page 150; specific examples can be found in Wintermantel page 161 ff. (PE, Hostalen Gur 812, Hochst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec). The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, such as promotion of healing and regeneration (for example, growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular) that are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% cristallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can, for example, be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), submicron (nanofillers as from precipitation, preferentially plate like aspect ratio >10, 10-50 nm, contents 0.5 to 5% by volume).

A specific example of a material with which experiments were performed was PLDLA 70/30 including 30% (weight percent) biphase Ca phosphate that showed a particularly advantageous liquefaction behaviour.

Material compositions and mixtures, for example compositions including Ca phosphate, may also be provided with—for example encapsulated—pharmaceutical substances for being released targetedly into the surrounding tissue. Such pharmaceutical substances may include growth promoting, antibiotic, anti-inflammatory and/or otherwise healing and/or preventing agents.

The material of the tool (for example, sonotrode) and/or the material of the auxiliary element may be any material that does not melt at the melting temperatures of the liquefiable material. Especially, the tool and/or the auxiliary element may be of a metal, for example a titanium alloy. A preferred material is titanium grade5. This material, in addition to being generally suited for implantable devices, has a comparably low heat conduction. Because of this low heat conduction, the melting zone arising in liquefiable material and at the interface to the directing structure is heated quickly, without the surroundings being heated to too high temperatures. Alternative materials for the tool and/or the auxiliary element are other metals like other titanium alloys, stainless steel, ceramics like Zirconium oxides or Aluminum oxides, or hard plastics such as PEEK etc.

The effect of low heat conduction away from the augmentation material may, as an alternative to using a material with low heat conduction for the tool, also be achieved by a coating of a low heat conduction material on a tool of an arbitrarily chosen material (metal), including steel or aluminum.

BRIEF DESCRIPTION OF THE DRAWINGS

In the following, ways to carry out the invention and embodiments are described referring to drawings. The drawings mostly are schematic. In the drawings, same reference numerals refer to same or analogous elements. The drawings show:

FIG. 1 bone tissue with an initial opening;

FIGS. 1a and 1b distal portions of opening forming sonotrodes;

FIG. 2a-8 arrangements including a tool (namely, a sonotrode), an augmentation element and/or an auxiliary element for segmented augmentation;

DESCRIPTION OF THE PREFERRED EMBODIMENTS

Figure 2C:
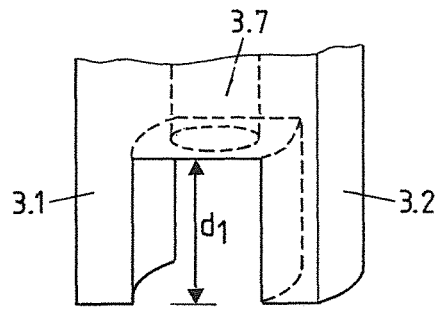

FIG. 1 shows a portion of bone tissue of a living human or animal bone. For example, the bone tissue may be jawbone tissue or bone tissue of other regions of the skull or may be bone tissue of the spinal column, such as of a vertebral body, or may be bone tissue of an extremity, or of a bone of the thorax, or of any other part of the human or animal bone framework. The depicted bone tissue includes comparably dense cortical bone 201 along the bone surface and less dense trabecular or spongy bone 202. An initial opening 203 in which an implant—such as, for example, a bone screw or a suture anchor—is to be anchored has, for example, been made by drilling. Alternatively, the initial opening 203 may be naturally present or may have been caused otherwise, for example in the course of a surgical operation. An opening axis 204 is shown. In case the opening is made by drilling, the opening may have rotational symmetry with respect to the axis 204. Because of the relatively low mechanical load resistance of the trabecular bone, especially if the bone is osteoporotic or osteopenic, it is desirable to augment the mechanical stability of the bone tissue prior to the implantation of the implant. According approaches have been described in WO 2010/045 751 incorporated herein by reference.

In accordance with a further, sixth, aspect of the invention, an initial opening 203 is made by a set-up in which a vibrating tool (sonotrode) or a counter element is also used as hole forming instrument.

Referring to FIGS. 1a and 1b, firstly the option of using the tool (for example, sonotrode) as hole forming element is discussed. For the purpose of forming the initial opening 203, the forward (distally) facing portions of the sonotrode are accordingly shaped. During introduction of the tool, the tool is forced into a distal direction while vibrations are coupled into the tool, wherein the parameters of the vibration are chosen to cause the distal end of the sonotrode to be forced into the bone tissue to cause an opening that is cylindrical or that in cross section is ring-shaped. This may be combined with a subsequent augmentation step in a 'rearward' configuration as, for example, described in WO 2010/045751 incorporated herein by reference, or as described for some embodiments hereinafter. More specifically, after the forcing step is finished, the sonotrode is again subject to mechanical oscillations—with accordingly adapted energy and other parameters—while it is retracted. At this time, proximally of the most distal sonotrode portion an augmentation element is placed and is at least in part liquefied by the simultaneous retraction and vibration energy impact.

FIGS. 1a and 1b show example of distal portions of a sonotrode 3. The distal portions include a distal broadening that forms a shoulder that is pressed against the augmentation element 1 in the augmentation step in which the sonotrode is subject to a pulling force, and the interface between the sonotrode (or, More particularly, the shoulder) and the augmentation element serves as the liquefaction interface. The distally facing portions of the sonotrode are equipped with a cutting edge 93 (FIG. 1a) and/or with a piercing tip 94 (FIG. 1b) configurations with a piercing tip 94 are especially suited in situations where the bone tissue is very weak and has little density and/or the diameter of the opening is comparably small.

In accordance with a second option, the instrument by which the initial opening is made or extended is not the tool that is later used for coupling the energy required for liquefaction into the augmentation element, but is the counter element for applying the counter force (in a forward configuration where the tool is held towards a distal direction while energy is coupled into the augmentation element for liquefying material of it). The counter element 2 in this may be shaped for example like the shown in FIG. 1*a*, FIG. 1*b* and described hereinbefore referring to the tool.

Alternatively, the step of forcing the counter element into the tissue may be carried out manually without any further energy source.

In embodiments according to the second option, the energy coupled into the augmentation element may as an alternative to mechanical energy also be radiation and/or heat.

For the forcing step and for the augmentation step, the vibration tool is coupled to a vibration source, in particular to a source of ultrasonic vibration (e.g., piezoelectric vibration generator possibly including a booster to which the tool is coupled) and the tool and is suitable for transmission of the vibration from the proximal tool end to the distal tool end, preferably such that a tool face—that faces to the proximal side and in contact with the augmentation element forms the liquefaction interface—vibrates with a maximal longitudinal amplitude. It is possible also to activate the tool to vibrate in a radial or in a rotational direction.

For the augmentation step, it is preferable to work with a substantially constant output of vibrational power, i.e. with vibration (base vibration) of substantially constant frequency and amplitude, wherein the frequency is in the above named frequency range (preferably between 2 and 200 kHz, between 10 and 100 kHz, or between 20 and 40 kHz) and is a resonant frequency of the vibrating system, and wherein the amplitude is in the range of 10 to 50 μm, preferably 20-40 μm. For the forcing step, in particular in cases in which the hard tissue constitutes a relatively high resistance, vibrational modes as known from, for example, vibration assisted bone cutting are preferable. Such vibration modes usually include pulses of higher amplitude and possibly sharper profiles (e.g., rectangular profile or Dirac impulse) and are, for example, provided by modulating the amplitude of the base vibration to, for example, form pulses of higher amplitude and preferably by also sharpening the input wave form as compared with the base vibration and by matching the system's resonance frequency. The so created pulses can include one or several wave cycles of the base vibration each, and can be periodic with a modulation frequency preferably in the range of 0.5-5 kHz or they can be generated stochastically (in amplitude and modulation frequency) but in any case in phase with the system's resonance frequency. A means for producing stochastically occurring pulses is described in the publication U.S. Pat. No. 7,172,420, which is incorporated herein by reference. Therein the higher amplitude of the pulses is preferably greater than the base vibration amplitude by a factor of between 2 and 10.

Alternatively, such pulses can be achieved by overlaying the base vibration or replacing it with a pulse excitation generated by a mechanical impulse generator (e.g., including a rotationally driven unbalanced mass or hammer). Therein the higher amplitude of the pulses is preferably again greater than the base vibration amplitude by a factor of between 2 and 10 and the pulse frequency which may be regular in the region of 20 to 200 Hz and in particular lower than the lowest resonance frequency of the vibrating system (e.g., undesired flexural vibration of the sonotrode). The low pulse frequencies are particularly important if material liquefaction during the forcing step is possible but is to be prevented as best as possible.

If as described above two different vibration modes are to be used in the forcing and in the anchoring step, the vibration source to which the vibration tool is coupled during the two steps is to be equipped for selectively producing the two vibration modes and with switching means for switching the vibration source from one vibration mode into the other one.

Referring to the following figures, methods of augmenting bone tissue of, for example, a configuration as shown in FIG. 1 are described. With reference to FIGS. 2-8, embodiments of segmented augmentation are described.

Figure 2D:
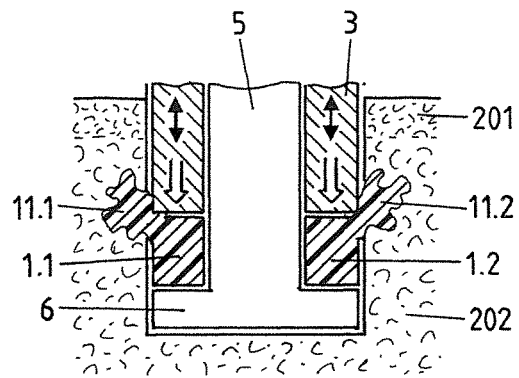
Figure 2E:
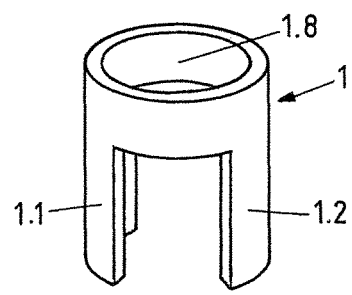
Figure 2F:
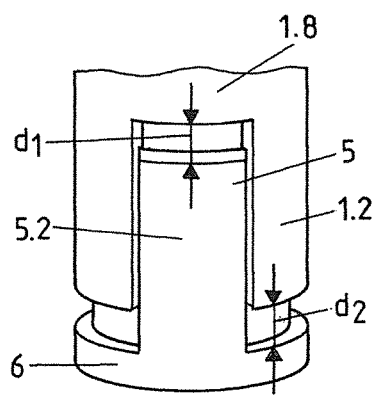
Figure 2G:
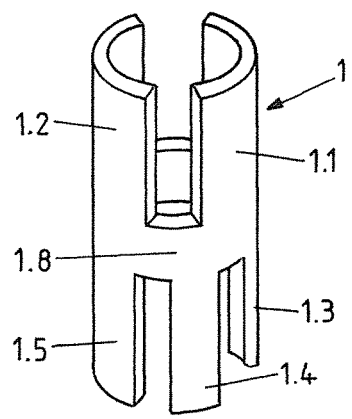

A first example of an assembly for circumferential segmentation is depicted, in sections along different planes, in FIGS. 2*a* and 2*b*. FIG. 2*c* shows a view of the sonotrode 3 of the assembly, FIG. 2*d* shows a schematic view of the assembly in section in the initial opening during the process, FIG. 2*e* shows a variant of an augmentation element, FIG. 2*f* shows the augmentation element of FIG. 2*e* together with a specially adapted auxiliary element, and FIG. 2*g* shows yet another augmentation element. FIG. 2*a* shows a cross section in plane A-A of FIG. 2*b*.

The assembly includes an augmentation element 1 that has two separate augmentation element portions 1.1, 1.2, a tool (sonotrode) 3, and an auxiliary element 2 serving as counter element. The auxiliary element forms a guiding shaft 5 and a distal broadening 6 that forms a shoulder so that the augmentation element is capable of being compressed between the sonotrode 3 and the shoulder 6 during the process. The guiding shaft in the depicted embodiment in other word forms part of a counter element that in addition to the guiding element shaft includes a distal broadening 6 with proximally (rearwardly) facing counter element contact faces through which a counter force is coupled into the augmentation element portions. The counter force is a force of equal magnitude but opposite direction to the force by which the sonotrode is pressed against the augmentation element portions.

The guiding shaft 5 does not have the shape of a rotational cylinder but is circumferentially structured to include two axial grooves in which the two augmentation element portions 1.1, 1.2 are placed. The sonotrode 3 is correspondingly segmented to include two pushing portions 3.1, 3.2 with a cross section approximately corresponding to the cross section of the augmentation element portions 1.1, 1.2. The sonotrode also includes a central cannulation 3.7 for the shaft portion 5 of the auxiliary element 2.

In alternative embodiments, the auxiliary element may lack the distal broadening and merely be a guiding pin. In these embodiments, the counter force opposite to the sonotrode pressing force may be exerted by the tissue against which the augmentation element is pressed, or an adhesion and/or friction force by which the augmentation element portions adhere to the guiding element, or a combination thereof. In addition or as an alternative, it is also possible to provide the shaft and the augmentation element with surface structure engaging with each other, such as small indentations of the shaft into which corresponding inner protrusions of the augmentation element protrude.

The segmentation of the augmentation element as illustrated with respect to FIGS. 2*a* and 2*b* may be over the full axial length of the augmentation element portions, or it may be partial, i.e., the segmentation my be restricted to certain axial positions whereas in other axial positions the augmentation element may include a portion 1.8 that surrounds the guiding shaft, so that the augmentation element is one-piece.

A first according example is shown in FIG. 2e, where the shaft surrounding portion 1.8 is at the proximal end of the augmentation element. By the construction of the augmentation element shown in FIG. 2e, towards the distal end of the augmentation element there are open gaps between the element portions 1.1, 1.2. This may optionally be combined with an auxiliary element having a distal end that has according projections 5.2 as illustrated in FIG. 2f that prevent liquefied portions of the thermoplastic material to be spread into circumferential directions and. More particularly, the dimensions of the open gaps and the projections 5.2 may be adapted to each other so that the distance $d_1$ is smaller than or approximately equal to the distance $d_2$.

Yet another embodiment of an augmentation element with portions 1.1-1.5 held together by a shaft surrounding portion 1.8 is shown in FIG. 2g. In this embodiment, the shaft surrounding portion is in an axially central position. Also the embodiment of FIG. 2g may optionally be used together with an auxiliary element of the kind depicted in FIG. 2f.

In FIG. 2b a proximodistal axis 4 is also depicted. In the configuration of FIGS. 2a-2g, the elements 1, 2, 3, of the assembly do not have circular symmetry around this axis.

For carrying out the method with segmented augmentation, the assembly of FIGS. 2a and 2b is placed in the initial opening with the axis 4 approximately parallel to the opening axis 204. Then the sonotrode 3 is pressed towards the distal side while mechanical oscillations are coupled into the tool and while the auxiliary element is held against the pressing force so that the augmentation element is compressed between the vibrating sonotrode and the auxiliary element. The vibration energy is chosen to be sufficient so that a melting process of the thermoplastic auxiliary element material sets in the forward movement of the sonotrode (and/or the rearward movement of the auxiliary element) causes the molten thermoplastic material to be pushed aside and into structures of the surrounding cancellous bone tissue. This is illustrated in FIG. 2d. The displaced thermoplastic material portions 11.1, 11.2 re-solidify and thereby augment the bone tissue. The process is, for example, continued until all augmentation element material has been liquefied and displaced and until the distal end faces of the pushing portions abut against the shoulder 6 formed by the distal broadening.

Because the augmentation element is segmented, i.e. includes two augmentation element portions at different angular positions with respect to the proximodistal axis, the thermoplastic material portions 11.1 remain separate and form two augmentation regions.

Whereas referring to FIGS. 2a-2d circumferential segmentation of the augmentation element has been described referring to a configuration to augment a circular hole and using two segmentation element portions in a symmetrical arrangement, various other embodiments are possible. For example, the two segmentation element portions need not be arranged symmetrically with respect to a symmetry plane as the illustrated embodiment, but other, asymmetrical arrangements are possible. Further, more than two segmentation element portions may be used (as, for example, in the lower part of the augmentation element of FIG. 2g), for example three, four, five, six or even more—all in a symmetrical or asymmetrical arrangement. Also, the augmented initial opening need not be circular but can have any other shape.

Figure 3A:
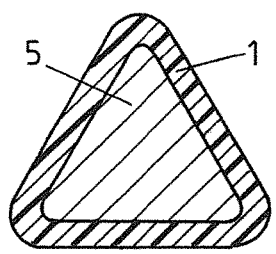
Figure 3B:
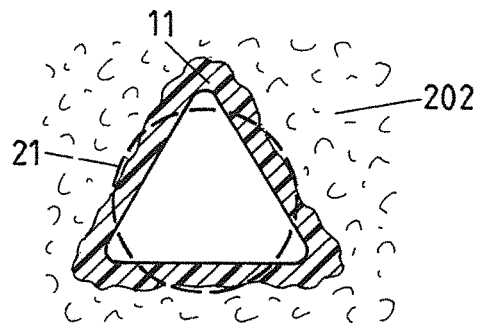
Figure 3C:
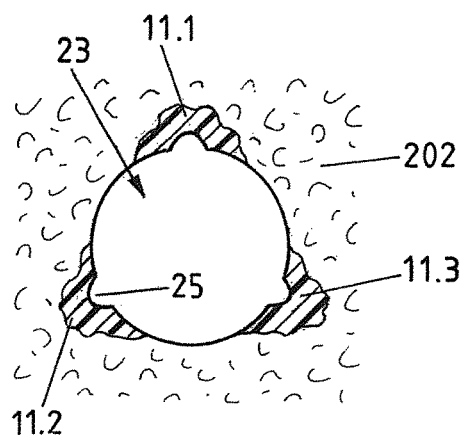
Figure 3D:
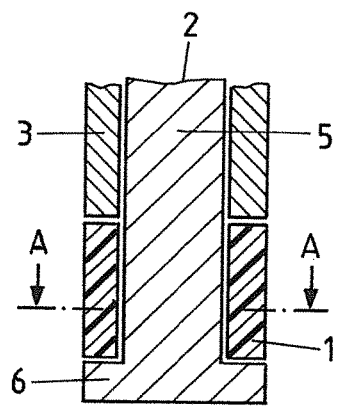
Figure 4:
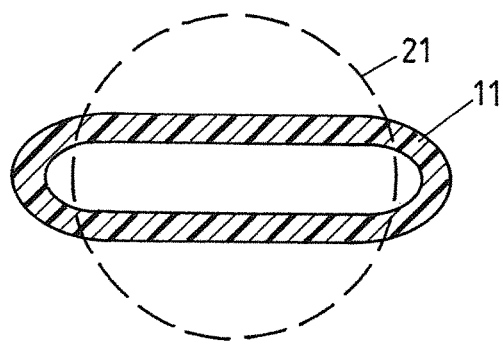

A further example of segmented augmentation is described referring to FIGS. 3a-4. This example uses the insight that the augmentation process does not rely on circular symmetry of the opening to be augmented. Rather, it is possible for mechanical energy capable of liquefying the thermoplastic augmentation element also in non-circular arrangements.

FIG. 3a shows, in cross section along plane A-A in FIG. 3d, a guiding shaft 5 of an auxiliary element, and an augmentation element 1 surrounding the guiding shaft 5. The guiding shaft and the augmentation element have a translational symmetry along the proximodistal axis and a generally triangular shape in cross section. The sonotrode 3 is proximal of the augmentation element and has a portion with a similar shape.

For augmentation, in a first step, the assembly of FIGS. 3a and 3d is placed in the initial opening. Then the sonotrode 3 is pressed towards the distal side while mechanical oscillations are coupled into the tool and while the auxiliary element is held against the pressing force so that the augmentation element is compressed between the vibrating sonotrode and the auxiliary element and so that at the interface between the sonotrode and the augmentation element the thermoplastic material of the augmentation element starts melting and is displaced into the surrounding bone tissue. The result is illustrated, again in section, in FIG. 3b. The initial opening, that is triangular in cross section, is surrounded by an augmented region where the bone tissue is interpenetrated by the augmentation material 11. The dashed line 21 in FIG. 3b shows where in a next step a bore is added. The bore 23 has a circular cross section and is thus suitable for implanting, in a subsequent step (not shown) a surgical screw. When the bore is made, further bone tissue as well as regions of the augmentation material are removed. What remains (FIG. 3c) is bone tissue that is augmented in the regions where the augmentation material is not removed. FIG. 3c illustrated three separated augmentation material portions 11.1, 11.2, 11.3. The lobes 25 that may optionally remain at the edges of the initial opening may add further flexibility and may soon after implantation of the surgical screw (or other implant) be filled by tissue.

As an alternative to being triangular, the initial opening and the augmentation element in variants of this group of embodiments may have other non-circular cross sections. An example of such an alternative is illustrated in FIG. 4, schematically in section perpendicular to the proximodistal axis. The initial opening and the augmentation element 1 have a generally elongate cross section, so that after augmentation and adding the bore (dashed line 21) two augmented regions will remain. Various other non-circular shapes are possible, both, symmetric and asymmetric. In particular, it is possible to adapt the shape to the anatomy of the place where the implant is to be anchored.

The approach of FIG. 4 can be implemented both, in forward configurations with a sonotrode 3 that is pushed during the augmentation process (as illustrated in FIG. 3d) and in "rearward" configurations in which the sonotrode is pulled, as for example described in WO 2010/045 751. In "rearward" configurations, further in accordance with the sixth aspect, the sonotrode may optionally have a cutting distal edge that allows manufacturing the initial opening by introduction of the sonotrode while mechanical energy is coupled into the sonotrode.

Figure 5A:
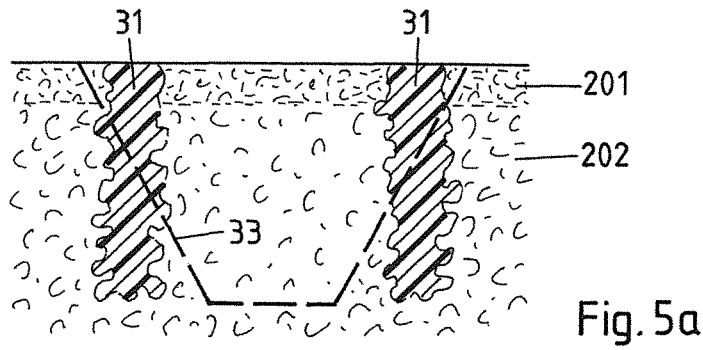
Figure 5B:
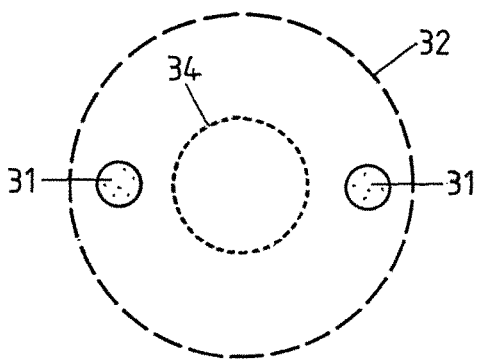

With reference to FIGS. 5a and 5b yet another possibility to provide segmented augmentation is depicted. FIG. 5a shows a section along the proximodistal axis, whereas FIG. 5b shows a view onto the tissue surface. In accordance with this possibility, the sequence of steps is reversed. As a further difference to the previously described embodiments, an auxiliary element with a guiding shaft is not required. Instead, a plurality of pin-like augmentation elements 31 are implanted in a first step. To this end, an according number of bores (initial openings) may be prepared, whereafter the pin-like augmentation elements 31, which consist of the thermoplastic material, are implanted. The pre-made bores may as an option have a depth that merely corresponds to the depth of the cortical bone tissue, i.e., the preparation then only includes locally removing the cortical bone. Alternatively, the pre-made bores may have a larger depth, or in case of weak bone or already-removed cortical bone, the augmentation elements may be directly driven into the bone tissue without any prior additional removal of bone tissue. Concerning the process of driving implants (here serving as augmentation elements) of thermoplastic material into bone tissue, it is referred to WO 02/06981 the content of which is incorporated herein by reference in its entirety.

The augmentation elements are implanted along the contour 32 of a bore 33 that is made subsequently to implanting the augmentation elements. The bore may be conical or have another shape with a cross section that diminishes as a function of the dept. More particularly, the cross section at the bone surface is such that the augmentation element is within the bore (dashed line 32 in FIG. 5*b*), and the cross section at the distal end of the bore (dotted line 34 in FIG. 5*b*) is such that at least part of the augmentation elements is outside of the bore. By this, not only a circumferential segmentation may be achieved but also a restriction of the augmented region to the deeper part of the bore so that for example no augmentation material reaches the top. This may be desired to make possible that after healing the cortical bone can be contiguous around the implant.

Figure 5C:
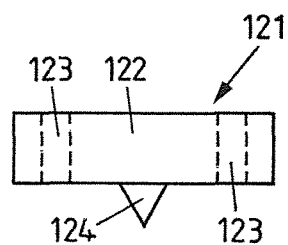
Figure 5D:
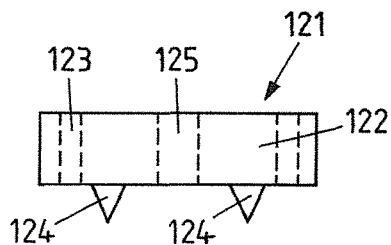

FIGS. 5*c* and 5*d* yet depict two versions of a guiding tool 121 for preparing bores for the augmentation process of FIGS. 5*a* and 5*b*. The tool 121 has a body 122 that in the depicted embodiments is essentially disk-like. The body has per augmentation element a guiding opening 123 for guiding a drill that pre-makes the holes and/or that guides the pin-like augmentation elements and sonotrode during the insertion of the augmentation elements. The tool may further include a holding structure 124 such as one or more spikes that secures the tool 121 against lateral movements. The embodiment of FIG. 5*d* further includes a central through opening 125 for the drilling of a centering bore for the later conical bore.

Whereas this embodiment has been described with a conical bore or a bore that has an otherwise tapering shape, the concept of implanting an augmentation element or a plurality of augmentation elements along a contour of a bore made subsequently may also be applied to cylindrical bores. In these embodiments, the outer contour of the bore should go through the implanted augmentation elements.

It is further also possible to combine a cylindrical bore with pin-like augmentation elements that are not implanted parallel to the proximodistal axis but radially outward (so that the distal end points away from the proximodistal axis). By such configuration, a similar effect as the one of the depicted embodiment may be achieved.

In the shown embodiment, two pin-like augmentation elements 31 are shown, however, the concept may also be realized with one or with more than two augmentation elements. Generally, a plurality of augmentation elements may be arranged in a symmetrical or in an asymmetrical configuration.

The effect of restricting the augmentation material to deeper regions of the bore by means of a tapering bore may also be used in configurations in which the augmentation material is applied by a method as described referring to FIGS. 1-4 or by variants thereof without segmentation (but, for example, with a tube-shaped augmentation element, including 'rearward' configurations as described in WO 2010/045751 incorporated herein by reference).

Figure 6:
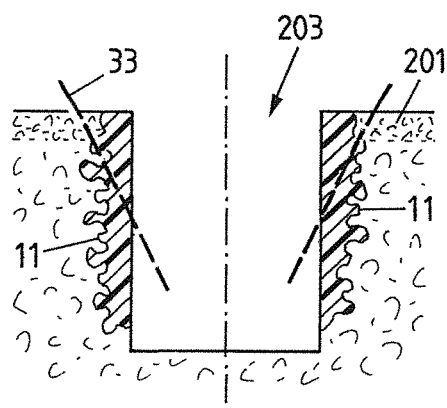

FIG. 6 shows, in cross section along the proximodistal axis, a configuration where an initial opening 203 of for example cylindrical shape has been augmented so that augmentation material portions 11 strengthen the bone tissue. This augmentation may be a segmented augmentation where the segmentation material is confined to certain angles around the circumference—for example as taught referring to previous figures—or may be a non-segmented augmentation where the augmentation material is distributed around the periphery. Subsequently, tissue and material may be removed along the dashed line 33 so that the augmented bone surface becomes restricted to the deeper regions of the opening.

Circumferential segmentation and depth dependence of the augmentation may be combined. An example is illustrated in FIGS. 7*a*-7*c*. The initial opening is stepped and has a large diameter proximal portion and a smaller diameter distal portion so that a shoulder 111 is formed. The guiding shaft 5 in cross section has a shape as illustrated in FIG. 7*c*. FIGS. 7*a* and 7*b* correspond to cross sections along planes that in the section only through the guiding shaft (FIG. 7*c*) correspond to the lines A-A and B-B, respectively. The augmentation element has first augmentation element portions 1.1, 1.2 that are positioned around at the periphery and that during the method step of liquefying are pressed against the shoulder. Second augmentation element portions 1.3, 1.4 are located distally in the channels 5.1 of the guiding shaft. During liquefaction, they are pressed against the bottom of the initial opening. The shape of the sonotrode 3 is accordingly adapted. As an alternative to the depicted configuration, the auxiliary element may include abutment protrusions that axially extend from the guiding shaft proximally of the shoulder 111 and/or a distal broadening of the kind illustrated in FIG. 2*b* so that the counterforce to the pressing force is not exerted by the tissue but by the auxiliary element.

FIG. 8 shows yet another example of segmented augmentation, again in cross section parallel to the proximodistal axis. The embodiment of FIG. 8 may combine axial segmentation (i.e. augmentation at different depths) with circumferential segmentation. In the embodiment of FIG. 8, the initial opening is tapered, it is for example conical. The auxiliary element 2 has an accordingly tapered shape. For the augmentation process, it is to be placed in the initial opening, with a circumferential wall and possibly a distal end in contact with bone tissue as shown in FIG. 8. The auxiliary element is a body with openings accessible from the proximal side. Between the openings and the circumferential wall, there are holes. For example, a larger, central opening 41 includes a plurality of holes 43 distributed regularly or irregularly around the periphery. Smaller, peripheral openings, for example, each include a lateral hole 43. The peripheral openings 42 may be distributed regularly or irregularly along the periphery. It would also be possible for the auxiliary element to include a single peripheral opening only. The augmentation elements 1 may, for example, be pin-shaped, with an outer diameter adapted to the dimension of the opening they are provided for. During the augmentation process, augmentation elements 1 are inserted in the openings and pressed towards the distal direction while mechanical energy impinges on the respective augmentation element. Thereby, the augmentation material at the distal end of the augmentation elements is liquefied and pressed out of the holes into the surrounding tissue.

The auxiliary element may be removed after liquefaction of the augmentation material; for example, removal may be made immediately after the offset of the mechanical energy input (for example the vibrations) so that the augmentation material is still soft in vicinity to the auxiliary element. As an alternative, a cutting element may be used for removing the auxiliary element; such cutting element may for example be a feature (proximally facing cutting edge or similar) adjacent to the holes 43 that cuts through the augmentation material portions that are at the interface between the auxiliary element 2 and the bone tissue.

In addition or as an alternative to the openings 41, 42, the auxiliary element—that may be viewed as guiding tool for individual augmentation elements 1 may have indentations (openings) along the circumferential surface. After an augmentation process using such an auxiliary element, thermoplastic augmentation material portions may protrude into the conical opening and thus need not be restricted to the bone tissue. Such embodiments are especially advantageous in situations where the subsequent implantation of the implant involves welding thermoplastic material of the implant to the augmentation material or involves an implant with a surface structure into which, when the augmentation material during implantation is again liquefied, again thermoplastic material may penetrate to generate a positive-fit connection. The principle of a positive-fit connection between a thermoplastic part (here: the augmentation element) and a non-liquefiable part having according structures is, for example, described in WO 2008/034 276 incorporated herein by reference; especially the basic principle is shown referring to FIGS. 1-7.

Next, embodiments of the aspect of impact/energy minimization are described. In these described embodiments, the energy coupled into the set-up during the process is mechanical vibration energy and the tool is a sonotrode. However, the concept can readily be expanded to other energy forms, including other mechanical energy (for example rotation), heat, electromagnetic radiation.

Figure 9A:
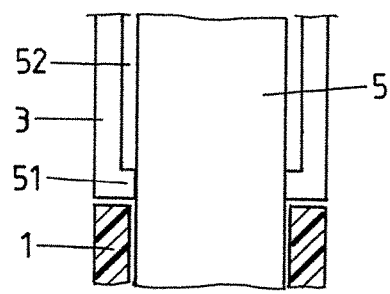
FIGS. 9a-20 concepts of augmentation with impact/energy minimization.
Figure 9B:
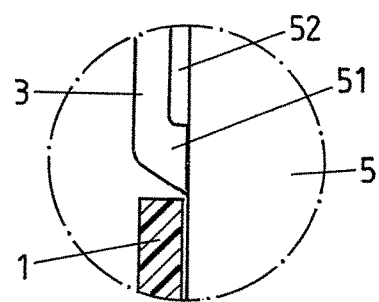

FIGS. 9*a* and 9*b*, in cross sections parallel to the proximodistal axis, show a first approach. It has been found that substantial noise and also possibly energy losses are caused by the contact between the sonotrode 3 and the guiding shaft 5 of the auxiliary element in configurations where the sonotrode and possibly also the augmentation element is/are guided by the guiding shaft. The region where the tool (sonotrode) and the auxiliary element slidingly overlap is also denoted "telescoping region" in the present text.

In FIGS. 9*a* and 9*b*, the inner diameter of the sonotrode is larger than the outer diameter of the guiding shaft so that a buffer volume 52 is formed around the guiding shaft. The sonotrode includes an inward projection 51 at the distal end thereof. The inward projection is, for example, an inwardly projecting ridge forming a contact surface in direct contact with the guiding shaft. The contact surface fully encompasses the shaft forming a sealing for liquefied material preventing the latter from penetrating into the buffer volume.

In the embodiment of FIG. 9*a*, the distal end face of the sonotrode that forms the contact with the augmentation element 1 is essentially flat and radial with respect to the axis, whereas the embodiment of FIG. 9*b* has a tapered sonotrode surface that helps to push the liquefied augmentation material outward into the surrounding tissue. In all embodiments, the contact face between the sonotrode and the augmentation element may generally have any shape, including flat, curved, tapered etc.

In the shown embodiment, the inward projection 51 is one-piece with the rest of the sonotrode. In alternative embodiments, a separate part—that can be viewed as a bushing—may be used. The use of such separate part may be advantageous, especially since a suitable material may be used. Such suitable material may be chosen so that it minimizes the sonotrode impact while it is not necessarily a good conductor for ultrasonic vibrations. An example of a suitable material for a bushing is PEEK; alternatively other polymer materials that have a comparably small friction coefficient to steel, such as PTFE, PA, etc. or other plastic or non-plastic materials may be used.

As a further option, the inward projection, especially if formed by a separate part (bushing), could include a small circumferential scraping lip in contact with the guiding shaft. As an alternative to such a scraping lip, also a corresponding fit allowing for a relative movement, such as a transition fit etc. may be used, especially for a hard-soft material combination between guiding shaft and projection/bushing 51.

In addition or as an alternative to the above-discussed variants, the buffer volume 52 may be partially or entirely filled by a material with reduced friction/noise development between the shaft and the vibrating (or directly heated or energy conducing) parts. Such material then may serve as a kind of inner liner; the material may for example be a polymer such as PEEK, PTFE, PA, etc.

Figure 10:
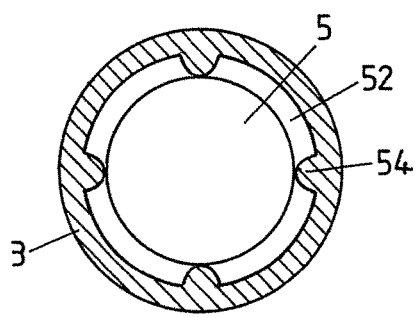
Figure 11:
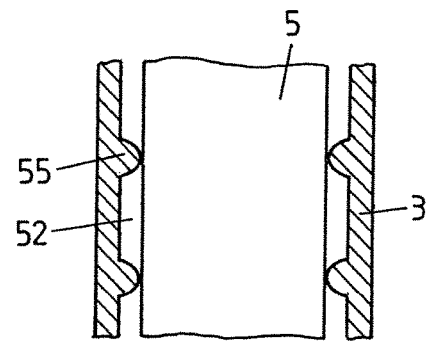

FIG. 10 depicts, in cross section perpendicular to the proximodistal axis, an embodiment where the sonotrode includes inwardly projecting axial ribs 54 so that again the contact surface between the sonotrode and the guiding shaft is diminished. This may optionally be combined with a distal inwardly projecting ridge as shown in FIGS. 9*a*, 9*b*. FIG. 11 (in cross section parallel to the proximodistal axis) similarly shows a configuration with inwardly projecting circumferential ribs 55. Again, a combination with the distal ridge is possible. Alternatively, instead of ribs or in addition thereto the sonotrode may include other inward projections such as humps etc.

FIGS. 9*a*-11, as well as FIGS. 17 and 18 described hereinafter, show examples of configurations where the area of the surface between the sonotrode and the auxiliary element is considerably reduced compared to configurations where the sonotrode is a cylindrical sleeve surrounding a cylindrical shaft. More particularly, in the telescoping region the contact surface is substantially (for example by at least a factor 2) smaller than the outer surface area of the auxiliary element in that telescoping region.

Another group of approaches for impact minimization, which may be combined with the approach of diminishing the direct contact between sonotrode and guiding shaft, is shown in FIGS. 12-15. The embodiments of these figures all include the concept that the augmentation element is shaped in a manner that causes the augmentation element, or at least portions thereof, to be liquefied with less energy impact, i.e., onset as a function of the energy that impinges on the augmentation element is earlier. This allows to reduce the power of the energy source, for example the power by which the sonotrode is operated.

Figure 12:
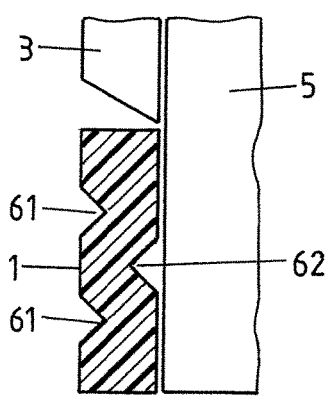
Figure 13:
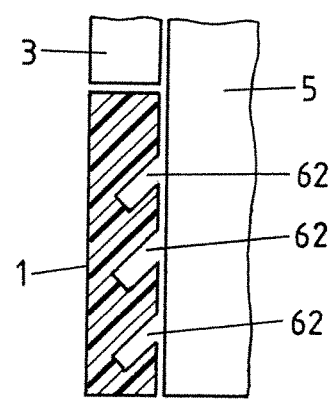

The cross sections of FIGS. 12 and 13 show a section of a generally rotationally symmetrical arrangement, with the symmetry axis (not shown) through the guiding shaft 5. The augmentation element 1 of FIG. 12 includes outer and inner grooves 61, 62, respectively, whereas the augmentation element of FIG. 13 has inner grooves 62. The grooves systematically weaken the augmentation element and, by causing necks, provide spots where the liquefaction upon absorption of the mechanical energy sets in first. Further, the inner grooves 62 of the embodiment of FIG. 13 are slanted towards the outside so that after onset of liquefaction at the necks the more proximal portions slide on the more distal portions and are forced outwardly, so that additional friction of not yet liquefied augmentation material with the lateral walls of the initial opening and/or an additional pressure onto the liquefied material is caused, both effects potentially assisting the augmentation process. A similar effect could be achieved by outer grooves that run along same conical surfaces as the illustrated embodiments, i.e. the grooves are such that after a liquefaction at the weak spots (necks) the more proximal parts of the augmentation element are subject to a shear movement that forces them outwardly when they are subject to pressure from the sonotrode 3. In both variants (and in combinations), an additional axial division (not shown in FIG. 13) or a circumferential segmentation as illustrated in previous embodiments may ensure sufficient flexibility for such an outward movement.

The grooves 61, 62 of the embodiments of FIGS. 12 and 13 or similar weakenings of the augmentation element 1 may also be chosen for not rotationally symmetrical arrangements, such as arrangements that include segmentation in accordance with any one of the embodiments described hereinbefore.

Figure 14:
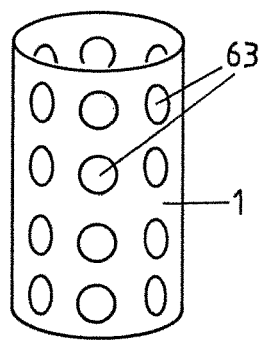
Figure 15:
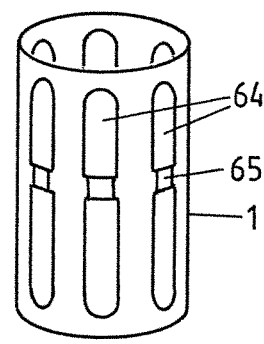

The embodiments of FIGS. 14 and 15 show views of other variants of systematically weakened augmentation elements. The embodiment of FIG. 14 includes an augmentation element 1 having generally a shape of a rotational cylinder with a plurality of through holes 63. In the depicted embodiment, the through holes are arranged in axial rows. Generally, the position and distribution of holes or other weakenings of the augmentation element may be chosen according to the needs.

In the embodiment of FIG. 15, the augmentation element 1 having generally a shape of a rotational cylinder includes elongate axial holes 64. The axial extension of such holes may be such as to correspond to a substantial portion (for example, at least ½ or even at least ⅔) of the axial length of the augmentation element 1. The axial holes, in addition to reducing the power requirements of the mechanical (or other) energy impact, may have the effect of causing a weak circumferential segmentation. The extension (along the circumferential direction) and the distribution of the axial elongate holes 64 may be chosen accordingly. In the depicted configuration, the augmentation element further includes bridge portions 65 that form bridges over the elongate holes, for example approximately in their middle, to enhance the mechanical stability of the augmentation element. Especially if a circumferential segmentation effect of the augmentation material is desired, the bridge portions 65 may have a minimal material strength only; for example, they may be thinner than the body of the augmentation element.

Figure 16:
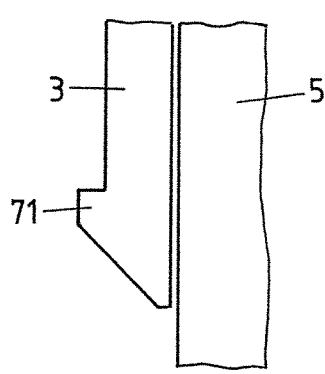

The embodiment of FIG. 16 (shown in section) includes a sonotrode 3 with an outwardly protruding (salient) distal feature 71 such as a circumferential ridge. Due to this shape, the sonotrode has a reduced thickness at more proximal positions so that it does not get into direct contact with the bone tissue proximally of the distal feature 71. This significantly reduces the impact, especially frictional heating of the adjacent bone tissue. The same applies if the tool 3 is not a sonotrode but a heating element or a rotating element.

An outwardly protruding distal feature of the kind illustrated in FIG. 16 may be realized in embodiments with a tapering contact face of the sonotrode to the augmentation element (as shown in FIG. 16), in embodiments with a flat contact face, or in combination with any other contact face shape. Combinations with the approaches of any one of the previous figures, including minimization of the contact surface between sonotrode and guiding shaft as illustrated in FIGS. 9-11 are possible.

Figure 17:
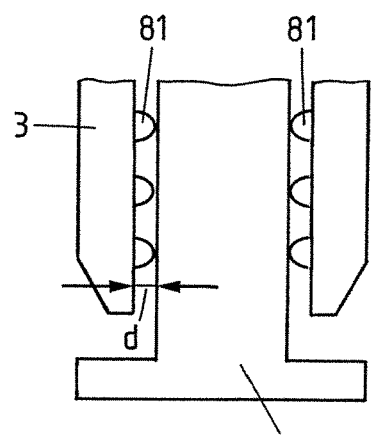

Another possibility of minimizing the sonotrode impact, especially the noise created by friction between sonotrode and guiding shaft, is shown in section in FIG. 17. The sonotrode in this embodiment includes a plurality of inwardly facing micro-protrusions 81. The micro-protrusions, which may be conical or calotte shaped or have other shapes, abut against the auxiliary element 2 guiding shaft and thereby cause the contact surface between the sonotrode 3 and the guiding shaft to be minimal. The micro-protrusions 81 have a height that is comparably small so that the resulting gap between the shaft and the sonotrode has a thickness d that is so small that due to surface tension substantially no liquefied thermoplastic material will penetrate into the gap. More particularly, the gap thickness d (approximately corresponding to the height of the protrusions) may be between 0.02 mm and 0.2 mm. In a gap having a thickness of this order of magnitude, no thermoplastic material will penetrate.

Whereas FIG. 17 shows the micro-protrusions being inwardly protruding features of the sonotrode, it would also be possible to provide according outwardly facing protrusions of the guiding shaft.

Figure 18:
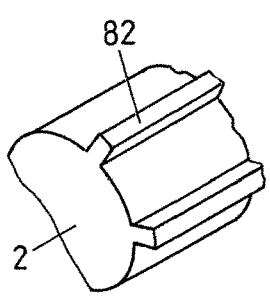

As an alternative to micro-protrusions that define punctiform contact surface portions, it would also be possible to have ridge-shaped micro-protrusions 82 as illustrated in FIG. 18. The embodiment of FIG. 18 includes the micro-protrusions 82 at the guiding shaft; of course, according (inwardly facing) ridge-shaped micro-protrusions may also be present at the sonotrode. The radial dimension of the protrusions of FIG. 18 may again be in the range between 0.02 mm and 0.2 mm.

Next, referring to all embodiments of the various aspects of the invention, some considerations on augmentation element dimensions, especially wall thickness are made. The thickness primarily depends on the desired infiltration depth (penetration depth), and on the porosity of the bone. First assuming that the augmentation element is tube-shaped and the radius of the augmentation element is much larger than the wall thickness—so that a plane configuration can be assumed in approximation, for an infiltration depth of 1 mm and a porosity of 40% (healthy bone in the present model), the wall thickness is 0.4 mm. For a porosity of 80% (osteoporotic bone in the present model), one gets a wall thickness of 0.8 mm for a penetration depth of 1 mm, and for a porosity of 60% one obtains 0.6 mm wall thickness. In the present approximation, the wall thickness is a linear function of the penetration depth, so that for example for a penetration depth of 2 mm and a porosity of 80%, the wall thickness has to be 1.6 mm. In these considerations, it is assumed that the material flow is ideal and that all augmentation element material is displaced into the bone tissue. In reality, this is not the case. Rather, the bone tissue promotes a freezing behavior of penetrating thermoplastic material, which freezing behavior is the more pronounced the denser the bone tissue. This effect can be taken into account by replacing the real, measured porosity by a reduced apparent porosity. The apparent porosity can be measured by the following process:

Augmentation using a simple augmentation cylinder of given wall thickness $d_w$ (for example 0.5 mm) in spongy bone, for example a pig's femoral condyle, complete displacing in penetration Measuring of an average penetration depth $d_m$ and a penetration height $h_m$ (corresponding to the axial extension of the augmented bone tissue portion)

Calculating a correction factor $F=d_m/d_t * h_s/h_m$ where $d_t$ denotes the theoretical penetration depth in accordance with the above considerations for ideal material flow and $h_s$ is the original height of the augmentation element, and Calculating an apparent porosity $P_A$ to be $P*F$.

In an example measurement with P=35%, the values of $d_m/d_t=0.6$ and $h_m/h_s=0.9$ have been obtained, so that F=0.667. For a porosity of 40% and a penetration depth of 1 mm one then obtains a wall thickness of 0.267 mm. The wall thickness is again proportional to both, the penetration depth and the porosity, so that starting from this value other wall thicknesses can be calculated.

If not all augmentation material is displaced into the bone tissue, residual wall thicknesses of material remaining within the augmented opening are to be added to the wall thickness.

In cases of segmented augmentation and/or augmentation elements with openings, along the axially running edges there will be additional material flow in circumferential directions to some extent. As a rule, polymer flow will broaden the augmented region (in circumferential direction) by about 0.5-1 mm. Thus, at these regions there will be an accordingly reduced infiltration depth. This is clinically not critical. Especially in dental medicine this will result in a reduced potential exposure of sensitive structures.

Figure 19:
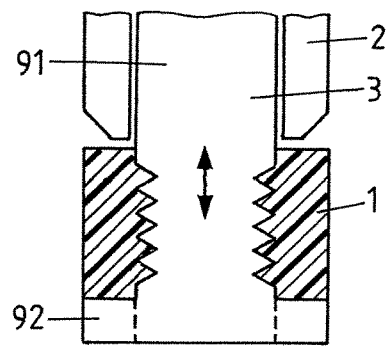

FIG. 19 shows, again in section, yet another approach of sonotrode impact minimization. In the embodiment of FIG. 19, the sonotrode 3 includes a sonotrode shaft 91 that is, at more proximal axial positions, encompassed by the auxiliary element 2 having the shape a sleeve. The augmentation element 1 is held by the sonotrode, for example in an interlocking connection. For example, the sonotrode 3 may have an outer thread, and the auxiliary element may be screwed onto the sonotrode. In the depicted configuration, the sonotrode has an—optional—distal broadening 92 (foot) that is an additional support securing the augmentation element against escaping in a distal direction. During the augmentation process, the sonotrode with the augmentation element affixed to it vibrates while the sleeve-like auxiliary element is pressed against the proximal surface of the augmentation element. At the interface between the sonotrode and the sleeve-like auxiliary element, mechanical energy is absorbed causing the augmentation element material to partially liquefy. During the process, for example the sonotrode's axial position may be held still while the auxiliary element 2 is pressed forward.

The embodiment of FIG. 19 features the advantage that due to the configuration with the central sonotrode and the peripheral auxiliary element, there is only minimal contact between the sonotrode and the tissue surrounding the initial opening.

An assembly corresponding to the one of FIG. 19 would also be possible in a 'forward' arrangement where the contact face between the augmentation element and the auxiliary element is at the distal end of the augmentation element. In such an assembly, the auxiliary element may for example have a thin shaft carrying a distal foot (that includes the contact face), the shaft reaching through the sonotrode. While such a configuration is a possibility, the configuration of FIG. 19 has the additional advantage of being more straightforward to implement.

Further, optionally, the distal end of the sonotrode could be provided with a cutting or piercing functionality, for example according to the sixth aspect of the invention. Such a piercing or cutting feature could for example work as a optionally vibration assisted awl when introducing the assembly in the tissue—the initial opening does then not need to be pre-made in a separate step but can be made by introducing the assembly.

Figure 20:
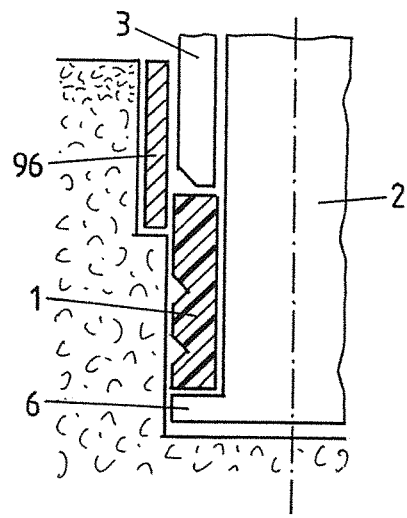

FIG. 20 shows in section an embodiment including a protecting element 96. The protection element at least partially encompasses the sonotrode 3 and thereby protects the bone tissue. The protection element 96 may include a distal cutting/reaming structure and/or a tapping structure to provide the augmented or not augmented bone tissue with a thread.

In the depicted configuration, the protecting element 96 is shown in combination with a stepped opening. This is not a requirement; sufficiently thin (<0.1 mm or 0.05 mm) protecting elements of sufficiently stiff material (for example steel) may also be used together with not stepped openings. A stepped opening may be provided in that the initial opening is made in a stepped fashion (for example using two drills of different diameters), or by a self-cutting structure of the protecting element itself, that then may for example also advance during the augmentation process to prevent all of the sonotrode with the possible exception of the most distal portion from getting into contact with the bone tissue.

A protecting element 96 could optionally be segmented in a circumferential direction and then optionally project further to the distal side, for example down to the bottom of the opening. Thereby, it locally masks the bone tissue and causes segmented augmentation. In this variant, the set-up of FIG. 20 is a further embodiment of the method according to its first aspect.

In an even further embodiment, a protecting element 96 serving as a mask could have a geometry of the kind illustrated for the augmentation element in FIGS. 14 and 15, i.e. include a body with a plurality of openings, especially in a segmented manner, i.e. comprising, as a function of the azimuthal angle, sections with openings and sections without openings. The openings in this even further embodiment may constitute a substantial portion of the surface of the element's convex hull, i.e. the empty spaces may constitute a substantial portion of for example at least 50%, at least 60% or at least $\frac{2}{3}$ of the surface of an imaginary cylinder of which the protecting element 96 forms the non-empty portions.

In all embodiments with a protecting element, (that may in some embodiments, as mentioned, serve as mask) the material of the protecting element may be a metal or a ceramic material. Because the surface of such material is repellant for liquefied thermoplastic material, the polymer will only weakly adhere to the protecting element so that the latter may be relatively easily be removed. This is even the case in configurations of the above-mentioned kind with openings through which the polymer material gets to the bone tissue—if the thickness of the protecting element is sufficiently thin, for example having a thickness of 0.1 mm or less.

In all embodiments with a protecting element, the protecting element may optionally be provided with an axial slit so that after removal of the shaft it may be radially collapsed and/or peeled off for removal.

The embodiments of FIG. 20 in addition may have the following optional features:
- the distal foot 6 that for example may protect a nerve underneath the initial opening;
- weakening grooves at the outside of the augmentation element 1.

In addition or as an alternative to protection from friction, an outer protection element 96 as shown in FIG. 20 may also serve other purposes. Especially, it may protect from heat conducted in the elements encompassed by the protection element 96. In addition, or as an alternative, it may itself take part in the energy conduction, for example by serving as a (ground) electrode for conducting electricity for the purpose of heating from the auxiliary element through the tool 3 or directly the augmentation element.

Figure 21:
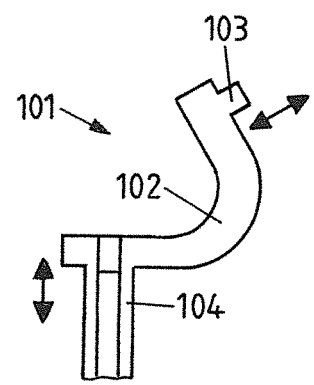
FIGS. 21-25 concepts of deflecting mechanical vibrations for an augmentation process.

According to yet another approach, the augmentation process may be combined with measures to deflect mechanical oscillations. A first approach is schematically illustrated in FIG. 21. FIG. 21 depicts a device 101 for deflecting mechanical oscillations including an elongate and bent oscillation element 102, so that the oscillation element 101 when excited to oscillate transversally at a coupling-in point oscillates transversally at a coupling-out point. The coupling-in point includes an input terminal 103 (that may be coupled to an oscillation source), and at the coupling-out point an output terminal 104 is formed, wherein a is provided with a sleeve-like terminal 104 that may either serve as the sonotrode (or a part thereof) or that may define an interface to the sonotrode. An auxiliary element that guides the augmentation element during the process may be guided in the center of the sleeve-like terminal 104. The device 101 at the region of the output terminal 104 may also include a through opening (cannulation) through which the auxiliary element may project and be held from its proximal side. While the embodiment of FIG. 20 does not readily allow for active application of a counter-force to the applied force by which the sonotrode is pressed against the distal direction, such active counter-force may not be necessary in cases where the tissue has enough strength to provide sufficient resistance.

Figure 22:
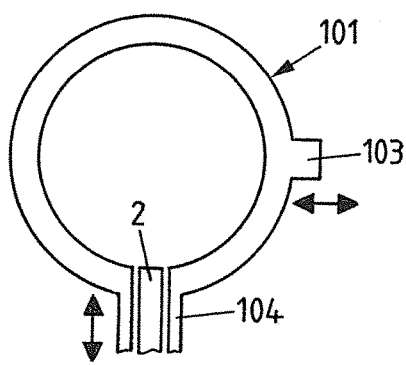

Yet another approach is depicted in FIG. 22. FIG. 22 illustrates a deflection device 101 that has a ring-shaped resonating body. The angle between the coupling-in port and the coupling-out point is an integer fraction of 360°. The coupling-out terminal 104 may again be sleeve-like. The auxiliary element 2 may be passively guided in an interior of the sleeve-like terminal 104. It may also be held by (not shown) elements that grip the auxiliary from outside of the plane defined by the ring-shaped resonating body.

Figure 23:
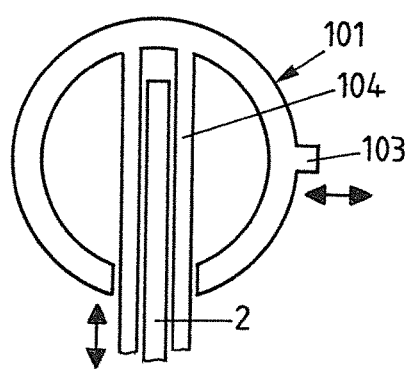

A variant of the embodiment of FIG. 22 is shown in FIG. 23. In contrast to the embodiment of FIG. 22, the coupling-out terminal 104 is attached to the inside of the ring and to its proximal (upper) portion.

In a variant of the embodiment of FIG. 23, the ring-shaped resonating body may be closed. The coupling-out terminal 104 may then project through a bore in the ring.

Figure 24:
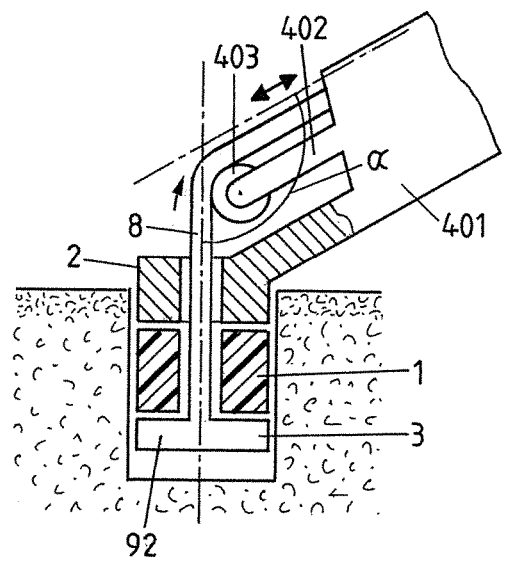

A further possibility of deflecting mechanical oscillations for inputting energy to liquefy at least portions of the augmentation element is shown in FIG. 24. FIG. 24 very schematically illustrates a "rearward" configuration, i.e. a configuration in which a tensile force is coupled into the tool—namely, the sonotrode 3—while energy is coupled into the tool and from there into the augmentation element 1.

In this configuration, the sonotrode has a distal broadening 92 (foot) that has a proximally facing coupling-out face that during the coupling of energy into the augmentation element 1 interfaces with a distal coupling-in face of the augmentation element 1. The sonotrode in addition has a cable 8 through that is connected to the distal broadening 92 and that connects the latter to a vibration source that in FIG. 24 is encased in the housing of a vibration generating apparatus 401. The cable 8 may, for example, be connected to a vibration generating module within the apparatus 401, which vibration generating module includes an ultrasonic transducer and is shiftable inside the housing so that during the process the cable can be pulled in the housing thereby pulling the distal broadening 92 towards the housing.

For deflecting the mechanical oscillations, the arrangement includes a deflection structure that in the depicted embodiment includes a mounting protrusion 402 with a deflection wheel 403 rotatingly mounted thereto. The counter element 2 (auxiliary element) is, in the embodiment of FIG. 24, also directly mounted to the housing of the apparatus 401. For augmentation, the arrangement with the apparatus 401, sonotrode 8, 92 and the augmentation element is positioned relative to the tissue so that the distal broadening 92 and, at least partially, the augmentation element 1 are placed in the tissue opening, and then the distal broadening is retracted towards a proximal direction by pulling the cable 8 while mechanical vibrations are coupled into the latter. The deflection structure serves for deflecting the mechanical vibrations by an angle that in the depicted configuration is at least approximately defined by the structure of the apparatus 401 with the counter element 2.

A configuration as illustrated in FIG. 24 may, for example, like the previously discussed concept, be advantageous for accessing tissue openings that would be difficult to access by an arrangement with movements only along a particular axis being possible, for example cavities resulting after a tooth extraction.

FIG. 24 also shows the deflection angle $\alpha$ (in this text, the deflection angle is defined in a manner that a deflection by 180° is no deflection).

Figure 25:
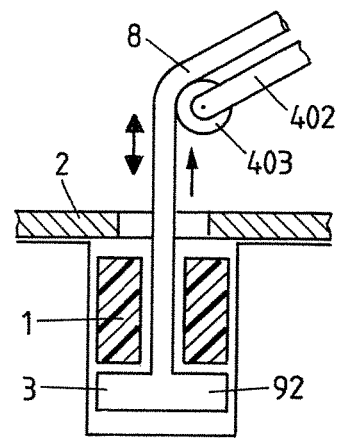

In the variant of FIG. 25, the counter element 2 is not mounted to the housing of the apparatus but is a separate part. In this configuration, the operator (surgeon, dentist) needs to position two different parts (namely, the apparatus and the counter element) but can choose the deflection angle freely and can vary it during the process. The deflection unit including the deflection wheel 403 may be mounted to the housing of the apparatus (may be part of the apparatus) or may be a separate part.

In embodiments where the deflection unit belongs to the apparatus, is readily possible to make the deflection unit extendible, i.e. to adjust the distance between the housing 401 and the deflecting element (the wheel 403 in the depicted configuration).

As an alternative to using a wheel, also a deflection edge, for example with a cable guiding channel may be used.

Figure 26:
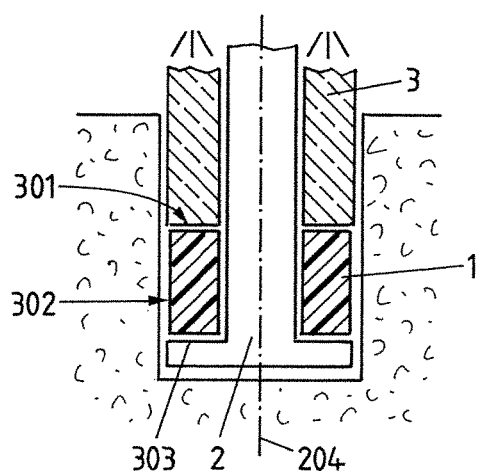
FIG. 26 the concept of using radiation for coupling energy into the augmentation element.

FIG. 26 schematically illustrates using a radiation source for coupling energy into the augmentation element 1 for the step of impinging the augmentation element with energy while the same is subject to a pressing force. To this end, the tool 3 is chosen to be a glass cylinder into which radiation is coupled from the proximal side. The auxiliary element 2 includes a foot interfacing with the distal end face of the augmentation element. The light coming in through the tool 3 may be absorbed at the distal end 301 of the tool 3, by the augmentation element (reference number 302), or at the surface 303 of the foot at the interface to the augmentation element.

Figure 27:
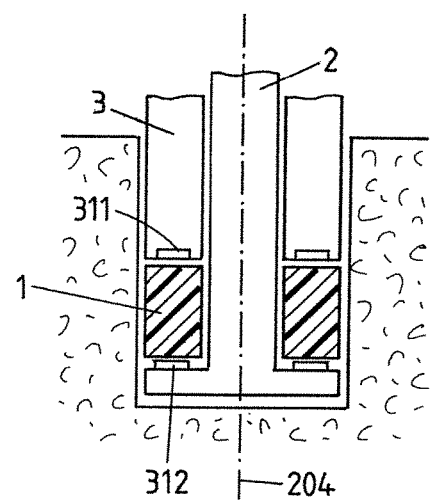
FIG. 27 the concept of using electricity for coupling energy into the augmentation element.

FIG. 27 shows an example of electricity conducted through the augmentation element 1 (which then includes an electrically conducting material with a relatively low conductivity). To this end, the tool 3 includes a first electrode 311 at the interface to the augmentation element 1 and the auxiliary element 2 includes a second electrode 312 at the interface to the augmentation element.

As an alternative, the tool 3 could be provided with a resistance heater capable of heating the interface to the augmentation element. Note that this is possible both in a forward configuration with a tool 3 as shown in FIG. 27 as well as in rearward configurations with a tool having the shape of the auxiliary element 2 of FIG. 27 and with a counter element for exerting a counter force, the counter element example having the shape of the tool of FIG. 3.

The configurations in FIGS. 26 and 27 may be symmetric about the axis 204 or may be formed as in examples of the hereinbefore described kind, especially in examples of segmented augmentation. The principle of radiation or electricity as energy source is further also applicable to other embodiments of the invention taught herein.

What is claimed is:

1. An assembly for augmenting hard tissue and/or hard tissue replacement material, the assembly comprising:
   a thermoplastic augmentation element having an augmentation element contact face;
   a tool with a contact face, the tool being configured to be pressed against the augmentation element contact face; and
   an auxiliary element having a guiding shaft, the augmentation element at least partially encompassing the guiding shaft;
   wherein the augmentation element at least partially encompassing the guiding shaft is configured:
      to be placed in an initial opening in in the hard tissue and/or hard tissue replacement material, with the tool in contact with a face of the augmentation element,
      and the tool is configured to be pressed against the augmentation element contact face while energy is coupled into the tool and while a periphery of a liquefaction interface of the tool and the augmentation element is within the opening, whereby material of the augmentation element at the liquefaction interface(s) is liquefied to yield liquefied material and to cause portions of the liquefied material to penetrate into structures of the hard tissue and/or hard tissue replacement material and to become, after hardening, augmentation material,
   the assembly further comprising an outer protection element configured to least partially encompass the tool and to thereby locally prevent the tool from being in contact with tissue.

2. The assembly according to claim 1, wherein the augmentation element is generally sleeve-shaped.

3. The assembly according to claim 1, wherein the protection element comprises a tap for cutting a thread.

4. The assembly according to claim 1, wherein the tool is a sonotrode equipped for being coupled to a source of mechanical vibrations.

5. The assembly according to claim 4, further comprising a vibration generating device coupled or equipped for being coupled to the sonotrode.

6. The assembly according to claim 1, wherein the tool is equipped for transmitting non-mechanical energy to the augmentation element contact face.

7. The assembly according to claim 1, wherein one if the auxiliary element and of the tool has a distal foot forming a proximally-facing shoulder and wherein the other one of the auxiliary element and the tool has a distally-facing contact face in contact with a proximal face of the augmentation element, whereby the augmentation element is compressible between the distally-facing contact face and the foot.

8. The assembly according to claim 1, wherein the auxiliary element is shaped for a portion of the augmentation element at least partially surrounding the guiding shaft, and the tool is shaped to be arranged proximally of the augmentation element at least partially surrounding the guiding shaft.

9. The assembly according to claim 8, wherein the tool comprises a protrusion facing radially inwardly towards the guiding shaft.

10. The assembly according to claim 9, wherein the protrusion is arranged at a distal end of the tool.

11. The assembly according to claim 8, wherein the augmentation element is sleeve shaped with at least a portion of the augmentation element completely surrounding the guiding shaft, and wherein the tool is sleeve shaped with a distal portion completely surrounding the guiding shaft.

12. The assembly according to claim 9, wherein the protrusion is an inwardly facing ridge.

13. The assembly according to claim 1, wherein the tool has a tapered distal end surface.

14. The assembly according to claim 1, wherein the protection element is metallic or of ceramic material.

15. The assembly according to claim 1, wherein the protection element is at least partially sleeve-shaped.

16. The assembly according to claim 1, wherein the tool comprises a radially outwardly projecting feature.

17. The assembly according to claim 16, wherein the radially outwardly projecting feature is a distal salient feature.

18. An assembly for augmenting hard tissue and/or hard tissue replacement material, the assembly comprising:
   a thermoplastic augmentation element having an augmentation element contact face;
   a tool with a contact face, the tool being configured to be pressed against the augmentation element contact face; and
   an auxiliary element having a guiding shaft, the augmentation element at least partially encompassing the guiding shaft;
   wherein the augmentation element at least partially encompassing the guiding shaft is configured:
      to be placed in an initial opening in in the hard tissue and/or hard tissue replacement material, with the tool in contact with a face of the augmentation element,
      and the tool is configured to be pressed against the augmentation element contact face while energy is coupled into the tool and while a periphery of a liquefaction interface of the tool and the augmentation element is within the opening, whereby material of the augmentation element at the liquefaction interface(s) is liquefied to yield liquefied material and to cause portions of the liquefied material to penetrate into structures of the hard tissue and/or hard tissue replacement material and to become, after hardening, augmentation material,
   wherein the tool comprises a distal broadening forming an salient feature that prevents a contact between the tool and the hard tissue and/or hard tissue replacement material at locations proximally of the salient feature.

19. An assembly for augmenting hard tissue and/or hard tissue replacement material, the assembly comprising:
   a thermoplastic augmentation element having an augmentation element contact face;
   a tool with a contact face, the tool being configured to be pressed against the augmentation element contact face; and
   an auxiliary element having a guiding shaft, the augmentation element at least partially encompassing the guiding shaft;
   wherein the augmentation element at least partially encompassing the guiding shaft is configured:

to be placed in an initial opening in in the hard tissue and/or hard tissue replacement material, with the tool in contact with a face of the augmentation element, and the tool is configured to be pressed against the augmentation element contact face while energy is coupled into the tool and while a periphery of a liquefaction interface of the tool and the augmentation element is within the opening, whereby material of the augmentation element at the liquefaction interface(s) is liquefied to yield liquefied material and to cause portions of the liquefied material to penetrate into structures of the hard tissue and/or hard tissue replacement material and to become, after hardening, augmentation material, wherein, in a telescoping region, a portion of the tool encompasses a portion of the auxiliary element or a portion of the auxiliary element encompasses the tool, wherein at least one of the tool and of the auxiliary element comprises at least one protrusion facing to the other one of the tool and the auxiliary element, whereby in the telescoping region a contact between the tool and the auxiliary element at locations different from the at least one protrusion is prevented.

\* \* \* \* \*